United States Patent
Patil et al.

(10) Patent No.: US 10,519,155 B2
(45) Date of Patent: Dec. 31, 2019

(54) 1,6-DIAZABICYCLO [3,2,1] OCTAN-7-ONE DERIVATIVES AND THEIR BACTERIAL INFECTIONS

(71) Applicant: WOCKHARDT LIMITED, Aurangabad (IN)

(72) Inventors: Vijaykumar Jagdishwar Patil, Solapur (IN); Ravikumar Tadiparthi, Aurangabad (IN); Bharat Dond, Aurangabad (IN); Amol Kale, Aurangabad (IN); Loganathan Velupillai, Aurangabad (IN); Deepak Dekhane, Maharashtra Pune (IN); Satish Shrimant Birajdar, Latur (IN); Mohammad Usman Shaikh, Shrirampur (IN); Sushilkumar Maurya, Maharashtra Aurangabad (IN); Piyush Ambalal Patel, Gujarat Anand (IN); Prasad Dixit, Maharashtra Aurangabad (IN); Mangesh Pawar, Maharashtra Aurangabad (IN); Mahesh Vithalbhai Patel, Aurangabad (IN); Sachin Bhagwat, M.S. Aurangabad (IN)

(73) Assignee: WOCKHARDT LIMITED, Chikalthana, Aurangabad (IN)

( * ) Notice: Subject to any disclaimer, the term of this patent is extended or adjusted under 35 U.S.C. 154(b) by 0 days.

(21) Appl. No.: 15/898,453

(22) Filed: Feb. 17, 2018

(65) Prior Publication Data

US 2018/0170930 A1 Jun. 21, 2018

Related U.S. Application Data

(63) Continuation of application No. 14/365,064, filed as application No. PCT/IB2013/053092 on Apr. 19, 2013, now abandoned.

(30) Foreign Application Priority Data

Aug. 25, 2012 (IN) .......... 2471/MUM/2012

(51) Int. Cl.
| | |
|---|---|
| *A61K 31/439* | (2006.01) |
| *C07D 471/08* | (2006.01) |
| *A61K 31/4545* | (2006.01) |
| *A61K 31/496* | (2006.01) |
| *A61K 31/55* | (2006.01) |
| *C07D 487/08* | (2006.01) |
| *A61K 31/407* | (2006.01) |
| *A61K 31/546* | (2006.01) |
| *A61K 45/06* | (2006.01) |
| *C07C 211/63* | (2006.01) |
| *A61P 31/04* | (2006.01) |

(52) U.S. Cl.
CPC .......... *C07D 471/08* (2013.01); *A61K 31/407* (2013.01); *A61K 31/439* (2013.01); *A61K 31/4545* (2013.01); *A61K 31/496* (2013.01); *A61K 31/546* (2013.01); *A61K 31/55* (2013.01); *A61K 45/06* (2013.01); *A61P 31/04* (2018.01); *C07C 211/63* (2013.01); *C07D 487/08* (2013.01)

(58) Field of Classification Search
CPC .................................................. A61K 31/439
See application file for complete search history.

(56) References Cited

U.S. PATENT DOCUMENTS

| | | | |
|---|---|---|---|
| 8,796,257 B2 * | 8/2014 | Maiti | C07D 519/00 514/210.21 |
| 2010/0087648 A1 | 4/2010 | Lampilas et al. | |

FOREIGN PATENT DOCUMENTS

| | | |
|---|---|---|
| DE | 10256976 A1 | 6/2004 |
| WO | WO1997042179 A1 | 11/1997 |
| WO | WO2009091856 A2 | 7/2009 |
| WO | WO2010024356 A1 | 3/2010 |

OTHER PUBLICATIONS

Jim O'Neil's publication, 2016. UK government report on antimicrobial resistance (AMR).
Nature Biotechnology vol. 36 No. 7 Jul. 2018, p. 555.

* cited by examiner

*Primary Examiner* — Bruck Kifle
(74) *Attorney, Agent, or Firm* — Bio Intellectual Property Services LLC (Bio IPS); O. (Sam) Zaghmout

(57) ABSTRACT

Compounds of Formula (I), their preparation and use in preventing or treating bacterial infections are disclosed.

Formula (I)

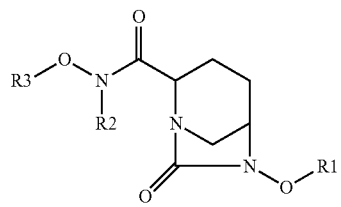

9 Claims, No Drawings

1,6-DIAZABICYCLO [3,2,1] OCTAN-7-ONE DERIVATIVES AND THEIR BACTERIAL INFECTIONS

CROSS-REFERENCE TO RELATED APPLICATIONS

This application is a Continuation of U.S. application Ser. No. 14/365,064, filed Jun. 12, 2014, which entered the National Phase of Ser. No. PCT/IB2013/053092, filed Apr. 19, 2013, which claims priority to Indian Application No. 2471/MUM/2012, filed Aug. 25, 2012. The entire disclosure of these prior applications are hereby incorporated by reference.

FIELD OF THE INVENTION

The invention relates to nitrogen containing compounds, use of these compounds as antibacterial agents, compositions comprising them and processes for their preparation.

BACKGROUND OF THE INVENTION

Emergence of bacterial resistance to known antibacterial agents is becoming a major challenge in treating bacterial infections. One way forward to treat bacterial infections, and especially those caused by resistant bacteria, is to develop newer antibacterial agents that can overcome the bacterial resistance. Coates et al. (Br. J. Pharmacol. 2007; 152(8), 1147-1154.) have reviewed novel approaches to developing new antibiotics. However, the development of new antibacterial agents is a challenging task. For example, Gwynn et al. (Annals of the New York Academy of Sciences, 2010, 1213: 5-19) have reviewed the challenges in the discovery of antibacterial agents.

Several antibacterial agents have been described in the prior art (for example, see PCT International Application Nos. PCT/US2010/060923, PCT/EP2010/067647, PCT/US2010/052109, PCT/US2010/048109, PCT/GB2009/050609, PCT/EP2009/056178 and PCT/US2009/041200). However, there remains a need for potent antibacterial agents for preventing and/or treating bacterial infections, including those caused by bacteria that are resistant to known antibacterial agents.

The inventors have surprisingly discovered nitrogen containing compounds with antibacterial properties.

SUMMARY OF THE INVENTION

Accordingly there are provided nitrogen containing compounds, methods for preparation of these compounds, pharmaceutical compositions comprising these compounds, and method for preventing or treating bacterial infection in a subject using these compounds.

In one general aspect, there are provided compounds of Formula (I):

Formula (I)

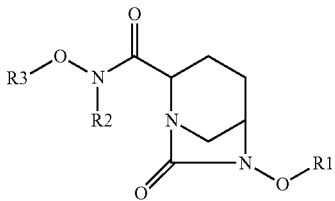

or a stereoisomer or a pharmaceutically acceptable salt thereof;
wherein:
$R_1$ is:
(a) $SO_3M$,
(b) $SO_2NH_2$,
(c) $PO_3M$,
(d) $CH_2COOM$,
(e) $CF_2COOM$,
(f) CHFCOOM, or
(g) $CF_3$;
M is hydrogen or a cation;
$R_2$ is:
(a) hydrogen,
(b) $(CH_2)_n$—$R_3$, or
(c) $COOR_3$,
n is 0, 1 or 2;
$R_3$ is:
(a) hydrogen,
(b) $C_1$-$C_6$ alkyl optionally substituted with one or more substituents independently selected from halogen, $OR_5$, CN, $COOR_5$, $CONR_6R_7$, $NR_6R_7$, $NR_5COR_8$, $NR_5CONR_6R_7$, heterocyclyl, heteroaryl, cycloalkyl or aryl,
(c) CN,
(d) $NR_6R_7$,
(e) $CONR_6R_7$,
(f) $NHCONR_6R_7$,
(g) aryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(h) heterocyclyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(i) heteroaryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(j) cycloalkyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(k) cycloalkyl substituted with $C_1$-$C_6$ alkyl wherein $C_1$-$C_6$ alkyl is further substituted with one or more substituents independently selected from $OR_5$, $NR_6R_7$, halogen, CN, or $CONR_6R_7$, or
(l) $OR_8$;
$R_4$ is:
(a) hydrogen,
(b) $C_1$-$C_6$ alkyl optionally substituted with one or more substituents independently selected from halogen, $OR_5$, CN, $COOR_5$, $CONR_6R_7$, $NR_6R_7$, $NR_5COR_8$, heterocyclyl, heteroaryl, cycloalkyl or aryl,
(c) aryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(d) heterocyclyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$, (e) heteroaryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$, or (f) cycloalkyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$;

$R_5$ and $R_8$ are each independently:
(a) hydrogen, or
(b) $C_1$-$C_6$ alkyl optionally substituted with one or more substituents independently selected from halogen, CN, $CONR_6R_7$, $NR_6R_7$, heterocyclyl, heteroaryl, cycloalkyl or aryl;

$R_6$ and $R_7$ are each independently:
(a) hydrogen,
(b) $C_1$-$C_6$ alkyl optionally substituted with one or more substituents independently selected from halogen, $OR_5$, CN, $COOR_5$, $CONR_5R_8$, $NR_5R_8$, $NR_5COR_8$, heterocyclyl, heteroaryl, cycloalkyl or aryl,
(c) aryl optionally substituted with one or more substituents independently selected from $C_1$-$C_6$ alkyl, $OR_5$, $NR_5R_8$, halogen, CN, $CONR_5R_8$, $SO_2$-alkyl, $SO_2$-aryl, $OSO_2$-alkyl, $OSO_2$-aryl, or $NHCONR_5R_8$,
(d) heterocyclyl optionally substituted with one or more substituents independently selected from $C_1$-$C_6$ alkyl, $OR_5$, $NR_5R_8$, halogen, CN, $CONR_5R_8$, $SO_2$-alkyl, $SO_2$-aryl, $OSO_2$-alkyl, $OSO_2$-aryl, or $NHCONR_5R_8$,
(e) heteroaryl optionally substituted with one or more substituents independently selected from $C_1$-$C_6$ alkyl, $OR_5$, $NR_5R_8$, halogen, CN, $CONR_5R_8$, $SO_2$-alkyl, $SO_2$-aryl, $OSO_2$-alkyl, $OSO_2$-aryl, or $NHCONR_5R_8$,
(f) cycloalkyl optionally substituted with one or more substituents independently selected from $C_1$-$C_6$ alkyl, $OR_5$, $NR_5R_8$, halogen, CN, $CONR_5R_8$, $SO_2$-alkyl, $SO_2$-aryl, $OSO_2$-alkyl, $OSO_2$-aryl, or $NHCONR_5R_8$, or
(g) $R_6$ and $R_7$ are joined together to form a four to seven member ring.

In another general aspect, there are provided pharmaceutical compositions comprising a compound of Formula (I), or a stereoisomer or a pharmaceutically acceptable salt thereof.

In another general aspect, there is provided a method for preventing or treating bacterial infection in a subject, said method comprising administering to said subject a pharmaceutically effective amount of a compound of Formula (I) or a stereoisomer or a pharmaceutically acceptable salt thereof.

In another general aspect, there is provided a method for preventing or treating a bacterial infection in a subject, said infection being caused by bacteria producing one or more beta-lactamase enzymes, wherein the method comprises administering to said subject a pharmaceutically effective amount of a compound of Formula (I) or a stereoisomer or a pharmaceutically acceptable salt thereof.

In another general aspect, there is provided a method for preventing or treating bacterial infection in a subject, said method comprising administering to said subject a pharmaceutically effective amount of a pharmaceutical composition comprising a compound of Formula (I) or a stereoisomer or a pharmaceutically acceptable salt thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising a compound of Formula (I) or a stereoisomer or a pharmaceutically acceptable salt thereof.

In another general aspect, there are provided pharmaceutical compositions comprising: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In another general aspect, there are provided pharmaceutical compositions comprising: (a) a compound of Formula (I), or a stereoisomer or a pharmaceutically acceptable salt thereof, and (b) at least one antibacterial agent or a pharmaceutically acceptable derivative thereof.

In another general aspect, there are provided pharmaceutical compositions comprising: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In another general aspect, there is provided a method for preventing or treating bacterial infection in a subject, said method comprising administering to said subject a pharmaceutically effective amount of a pharmaceutical composition comprising: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In another general aspect, there is provided a method for preventing or treating bacterial infection in a subject, said method comprising administering to said subject a pharmaceutically effective amount of a pharmaceutical composition comprising: (a) a compound of Formula (I), or a stereoisomer or a pharmaceutically acceptable salt thereof, and (b) at least one antibacterial agent or a pharmaceutically acceptable derivative thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising: (a) a compound of Formula (I), or a stereoisomer or a pharmaceutically acceptable salt thereof, and (b) at least one antibacterial agent or a pharmaceutically acceptable derivative thereof.

In another general aspect, there is provided a method for preventing or treating bacterial infection in a subject, said method comprising administering to said subject a pharmaceutically effective amount of a pharmaceutical composition comprising: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In another general aspect, there is provided a method for preventing or treating bacterial infection in a subject, said method comprising administering to said subject a pharmaceutically effective amount of: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In another general aspect, there is provided a method for preventing or treating a bacterial infection in a subject, said method comprising administering to said subject a pharmaceutically effective amount of: (a) a compound of Formula (I), or a stereoisomer or a pharmaceutically acceptable salt thereof, and (b) at least one antibacterial agent or a pharmaceutically acceptable derivative thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of: (a) a compound of Formula (I), or a stereoisomer or a pharmaceutically acceptable salt thereof, and (b) at least one antibacterial agent or a pharmaceutically acceptable derivative thereof.

In another general aspect, there is provided a method for preventing or treating bacterial infection in a subject, said method comprising administering to said subject a pharmaceutically effective amount of: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In another general aspect, there are provided methods for increasing antibacterial effectiveness of a antibacterial agent in a subject, said method comprising co-administering said antibacterial agent or a pharmaceutically acceptable derivative thereof with a pharmaceutically effective amount of a compound of Formula (I) or a stereoisomer or a pharmaceutically acceptable salt thereof.

The details of one or more embodiments of the invention are set forth in the description below. Other features, objects and advantages of the invention will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention. It must be noted that, as used in this specification and the appended claims, the singular forms "a," "an," and "the" include plural referents unless the content clearly dictates otherwise. All references including patents, patent applications, and literature cited in the specification are expressly incorporated herein by reference in their entirety.

The inventors have surprisingly discovered novel nitrogen containing compounds having antibacterial properties.

The term "$C_1$-$C_6$ alkyl" as used herein refers to branched or unbranched acyclic hydrocarbon radical with 1 to 6 carbon atoms. Typical, non-limiting examples of "$C_1$-$C_6$ alkyl" include methyl, ethyl, n-propyl, iso-propyl, n-butyl, iso-butyl, tert-butyl, n-pentyl, iso-pentyl, n-hexyl and the like. The "$C_1$-$C_6$ alkyl" may be unsubstituted, or substituted with one or more substituents. Typical, non-limiting examples of such substituents include halogen, alkoxy, CN, COOH, $CONH_2$, OH, —$NH_2$, —$NHCOCH_3$, cycloalkyl, heterocyclyl, heteroaryl, aryl and the like.

The term "cycloalkyl" as used herein refers to three to seven member cyclic hydrocarbon radicals. The cycloalkyl group optionally incorporates one or more double or triple bonds, or a combination of double bonds and triple bonds, but which is not aromatic. Typical, non-limiting examples of cycloalkyl groups include cyclopropane, cyclobutane, cyclopentane, cyclohexane, and cycloheptane. The cycloalkyl may be unsubstituted, or substituted with one or more substituents. Typical, non-limiting examples of such substituents include $C_1$-$C_6$ alkyl, halogen, alkoxy, CN, COOH, $CONH_2$, OH, $NH_2$, $NHCOCH_3$, heterocyclyl, heteroaryl, aryl, $SO_2$-alkyl, $SO_2$-aryl, $OSO_2$-alkyl, —$OSO_2$-aryl and the like.

The term "heterocyclyl" as used herein refers to four to seven member cycloalkyl group containing one or more heteroatoms selected from nitrogen, oxygen or sulfur. The heterocycloalkyl group optionally incorporates one or more double or triple bonds, or a combination of double bonds and triple bonds, but which is not aromatic. Typical, non-limiting examples of heterocycloalkyl groups include azetidine, pyrrolidine, 2-oxo-pyrrolidine, imidazolidin-2-one, piperidine, oxazine, thiazine, piperazine, piperazin-2,3-dione, morpholine, thiamorpholine, azapane, and the like. The heterocycloalkyl may be unsubstituted, or substituted with one or more substituents. Typical, non-limiting examples of such substituents include $C_1$-$C_6$ alkyl, halogen, alkoxy, CN, COOH, $CONH_2$, OH, $NH_2$, $NHCOCH_3$, heterocyclyl, heteroaryl, aryl, $SO_2$-alkyl, $SO_2$-aryl, $OSO_2$-alkyl, $OSO_2$-aryl and the like.

The term "aryl" as used herein refers to a monocyclic or polycyclic aromatic hydrocarbon. Typical, non-limiting examples of aryl groups include phenyl, naphthyl, anthracenyl, fluorenyl, phenanthrenyl, and the like. The aryl group may be unsubstituted, or substituted with one or more substituents. Typical, non-limiting examples of such substituents include $C_1$-$C_6$ alkyl, halogen, alkoxy, CN, COOH, $CONH_2$, OH, $NH_2$, $NHCOCH_3$, heterocyclyl, heteroaryl, aryl, $SO_2$-alkyl, $SO_2$-aryl, $OSO_2$-alkyl, $OSO_2$-aryl and the like.

The term "heteroaryl" as used herein refers to a monocyclic or polycyclic aromatic hydrocarbon group wherein one or more carbon atoms have been replaced with heteroatoms selected from nitrogen, oxygen, and sulfur. If the heteroaryl group contains more than one heteroatom, the heteroatoms may be the same or different. Typical, non-limiting example of heteroaryl groups include 1,2,4-oxadiazol, 1,3,4-oxadiazol, 1,3,4-thiadiazol, 1,2,3,4-tetrazol, 1,3-oxazol, 1,3-thiazole, pyridine, pyrimidine, pyrazine, pyridazine, furan, pyrrol, thiophene, imidazole, pyrazole, benzofuran, benzothiophene, benzimidazole, benzoxazole, benzothiazole, thiazole, and the like. The heteroaryl group may be unsubstituted, or substituted with one or more substituents. Typical, non-limiting examples of such substituents include $C_1$-$C_6$ alkyl, halogen, alkoxy, CN, COOH, $CONH_2$, OH, $NH_2$, $NHCOCH_3$, heterocyclyl, heteroaryl, aryl, $SO_2$-alkyl, $SO_2$-aryl, $OSO_2$-alkyl, $OSO_2$-aryl and the like.

The term "stereoisomers" as used herein refers to compounds that have identical chemical constitution, but differ with regard to the arrangement of their atoms or groups in space. The compounds of Formula (I) may contain asymmetric or chiral centers and, therefore, exist in different stereoisomeric forms. It is intended, unless specified otherwise, that all stereoisomeric forms of the compounds of Formula (I) as well as mixtures thereof, including racemic mixtures, form part of the present invention. In addition, the present invention embraces all geometric and positional isomers (including cis and trans-forms), as well as mixtures thereof, are embraced within the scope of the invention. In general, a reference to a compound is intended to cover its stereoisomers and mixture of various stereoisomers.

The term "optionally substituted" as used herein means that substitution is optional and therefore includes both unsubstituted and substituted atoms and moieties. A "substituted" atom or moiety indicates that any hydrogen on the designated atom or moiety can be replaced with a selection from the indicated substituent group, provided that the normal valency of the designated atom or moiety is not exceeded, and that the substitution results in a stable compound.

The term "pharmaceutically acceptable salt" as used herein refers to one or more salts of a given compound which possesses the desired pharmacological activity of the free compound and which are neither biologically nor otherwise undesirable. In general, the "pharmaceutically acceptable salts" refer to salts that are suitable for use in contact with the tissues of human and animals without undue toxicity, irritation, allergic response and the like, and are commensurate with a reasonable benefit/risk ratio. Pharmaceutically acceptable salts are well known in the art. For example, S. M. Berge, et al. (J. Pharmaceutical Sciences, 66: 1-19 (1977)), incorporated herein by reference in its entirety, describes various pharmaceutically acceptable salts in details.

In general, the compounds according to the invention contain basic (e.g. nitrogen atoms) as well as acid moieties (e.g. compounds of Formula (I) wherein M is hydrogen). A person of skills in the art would appreciate that such compounds, therefore, can form acidic salts (formed with inorganic and/or organic acids), as well as basic salts (formed with inorganic and/or organic bases). Such salts can be prepared using procedures described in the art. For example, the basic moiety can be converted to its salt by treating a compound with a suitable amount of acid. Typical, non-limiting examples of such suitable acids include hydrochloric acid, trifluoroacetic acid, methanesulphonic acid, or the like. Alternatively, the acid moiety may be converted into its salt by treating with a suitable base. Typical non-limiting examples of such bases include sodium carbonate, sodium bicarbonate, potassium carbonate, potassium bicarbonate or the like. In case of compounds containing more than one functional groups capable of being converted into salt, each such functional group may be converted to salt independently. For example, in case of compounds containing two basic nitrogen atoms, one basic nitrogen can form salt with one acid while the other basic nitrogen can form salt with another acid. Some compounds according to the invention contain both, acidic as well as basic moieties, and thus can form inner salts or corresponding zwitterions. In general, all pharmaceutically acceptable salt forms of compounds of Formula (I) according to invention including acid addition salts, base addition salts, zwitterions or the like are contemplated to be within the scope of the present invention and are generically referred to as pharmaceutically acceptable salts.

The term "halogen" or "halo" as used herein refers to chlorine, bromine, fluorine, or iodine.

The term "infection" or "bacterial infection" as used herein includes presence of bacteria, in or on a subject, which, if its growth were inhibited, would result in a benefit to the subject. As such, the term "infection" in addition to referring to the presence of bacteria also refers to normal flora, which is not desirable. The term "infection" includes infection caused by bacteria.

The term "treat", "treating" or "treatment" as used herein refers to administering a medicament, including a pharmaceutical composition, or one or more pharmaceutically active ingredients, for prophylactic and/or therapeutic purposes. The term "prophylactic treatment" refers to treating a subject who is not yet infected, but who is susceptible to, or otherwise at a risk of infection (preventing the bacterial infection). The term "therapeutic treatment" refers to administering treatment to a subject already suffering from infection. The terms "treat", "treating" or "treatment" as used herein also refer to administering compositions or one or more of pharmaceutically active ingredients discussed herein, with or without additional pharmaceutically active or inert ingredients, in order to: (i) reduce or eliminate either a bacterial infection or one or more symptoms of the bacterial infection, or (ii) retard the progression of a bacterial infection or of one or more symptoms of the bacterial infection, or (iii) reduce the severity of a bacterial infection or of one or more symptoms of the bacterial infection, or (iv) suppress the clinical manifestation of a bacterial infection, or (v) suppress the manifestation of adverse symptoms of the bacterial infection.

The term "pharmaceutically effective amount" or "therapeutically effective amount" or "effective amount" as used herein refers to an amount, which has a therapeutic effect or is the amount required to produce a therapeutic effect in a subject. For example, a therapeutically or pharmaceutically effective amount of an antibacterial agent or a pharmaceutical composition is the amount of the antibacterial agent or the pharmaceutical composition required to produce a desired therapeutic effect as may be judged by clinical trial results, model animal infection studies, and/or in vitro studies (e.g. in agar or broth media). The pharmaceutically effective amount depends on several factors, including but not limited to, the microorganism (e.g. bacteria) involved, characteristics of the subject (for example height, weight, sex, age and medical history), severity of infection and the particular type of the antibacterial agent used. For prophylactic treatments, a therapeutically or prophylactically effective amount is that amount which would be effective in preventing a microbial (e.g. bacterial) infection.

The term "administration" or "administering" includes delivery of a composition or one or more pharmaceutically active ingredients to a subject, including for example, by any appropriate methods, which serves to deliver the composition or its active ingredients or other pharmaceutically active ingredients to the site of the infection. The method of administration may vary depending on various factors, such as for example, the components of the pharmaceutical composition or the nature of the pharmaceutically active or inert ingredients, the site of the potential or actual infection, the microorganism involved, severity of the infection, age and physical condition of the subject and a like. Some non-limiting examples of ways to administer a composition or a pharmaceutically active ingredient to a subject according to this invention includes oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash. In case of a pharmaceutical composition comprising more than one ingredient (active or inert), one of way of administering such composition is by admixing the ingredients (e.g. in the form of a suitable unit dosage form such as tablet, capsule, solution, powder and a like) and then administering the dosage form. Alternatively, the ingredients may also be administered separately (simultaneously or one after the other) as long as these ingredients reach beneficial therapeutic levels such that the composition as a whole provides a synergistic and/or desired effect.

The term "growth" as used herein refers to a growth of one or more microorganisms and includes reproduction or population expansion of the microorganism (e.g. bacteria). The term also includes maintenance of on-going metabolic processes of a microorganism, including processes that keep the microorganism alive.

The term, "effectiveness" as used herein refers to ability of a treatment or a composition or one or more pharmaceutically active ingredients to produce a desired biological effect in a subject. For example, the term "antibacterial effectiveness" of a composition or an antibacterial agent refers to the ability of the composition or the antibacterial agent to prevent or treat the microbial (e.g. bacterial) infection in a subject.

The term "synergistic" or "synergy" as used herein refers to the interaction of two or more agents so that their combined effect is greater than their individual effects.

The term "antibacterial agent" as used herein refers to any substance, compound or a combination of substances or a combination compounds capable of: (i) inhibiting, reducing or preventing growth of bacteria; (ii) inhibiting or reducing ability of a bacteria to produce infection in a subject; or (iii) inhibiting or reducing ability of bacteria to multiply or remain infective in the environment. The term "antibacterial agent" also refers to compounds capable of decreasing infectivity or virulence of bacteria.

The term "beta-lactam antibacterial agent" as used herein refers to compounds with antibacterial properties and containing a beta-lactam nucleus in their molecular structure.

The term "beta-lactamase" as used herein refers to any enzyme or protein or any other substance that breaks down a beta-lactam ring. The term "beta-lactamase" includes enzymes that are produced by bacteria and have the ability to hydrolyze the beta-lactam ring in a beta-lactam compound, either partially or completely.

The term "beta-lactamase inhibitor" as used herein refers to a compound capable of inhibiting activity of one or more beta-lactamase enzymes, either partially or completely.

The term "pharmaceutically inert ingredient" or "carrier" or "excipient" refers to a compound or material used to facilitate administration of a compound, including for example, to increase the solubility of the compound. Typical, non-limiting examples of solid carriers include, starch, lactose, dicalcium phosphate, sucrose, and kaolin and so on. Typical, non-limiting examples of liquid carriers include, sterile water, saline, buffers, non-ionic surfactants, and edible oils such as oil, peanut and sesame oils and so on. In addition, various adjuvants commonly used in the art may be included. These and other such compounds are described in the literature, for example, in the Merck Index (Merck & Company, Rahway, N.J.). Considerations for inclusion of various components in pharmaceutical compositions are described, for example, in Gilman et al. (Eds.) (1990); Goodman and Gilman's: The Pharmacological Basis of Therapeutics, 8th Ed., Pergamon Press., which is incorporated herein by reference in its entirety.

The term "subject" as used herein refers to vertebrate or invertebrate, including a mammal. The term "subject" includes human, animal, a bird, a fish, or an amphibian. Typical, non-limiting examples of a "subject" includes humans, cats, dogs, horses, sheep, bovine cows, pigs, lambs, rats, mice and guinea pigs.

The term "pharmaceutically acceptable derivative" as used herein refers to and includes any pharmaceutically acceptable salt, pro-drugs, metabolites, esters, ethers, hydrates, polymorphs, solvates, complexes, enantiomers or adducts of a compound described herein which, upon administration to a subject, is capable of providing (directly or indirectly) the parent compound. For example, the term "antibacterial agent or a pharmaceutically acceptable derivative thereof" includes all derivatives of the antibacterial agent (such as salt, pro-drugs, metabolites, esters, ethers, hydrates, polymorphs, solvates, complexes, enantiomers or adducts) which, upon administration to a subject, is capable of providing (directly or indirectly) the antibacterial compound.

In general, the term "cation" includes Na, K, Mg, Ca, $NH_4^+$, $(CH_3CH_2)_3N^+$ etc.

In one general aspect, there are provided compounds of Formula (I):

Formula (I)

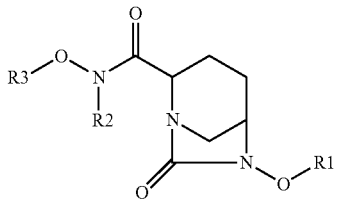

or a stereoisomer or a pharmaceutically acceptable salt thereof;
wherein:
$R_1$ is:
(a) $SO_3M$,
(b) $SO_2NH_2$,
(c) $PO_3M$,
(d) $NHCOCH_3$,
(e) $CF_2COOM$,
(f) $CHFCOOM$, or
(g) $CF_3$;
M is hydrogen or a cation;
$R_2$ is:
(a) hydrogen,
(b) $(CH_2)_n$—$R_3$, or
(c) $COOR_3$;
n is 0, 1 or 2;
$R_3$ is:
(a) hydrogen,
(b) $C_1$-$C_6$ alkyl optionally substituted with one or more substituents independently selected from halogen, $OR_5$, CN, $COOR_5$, $CONR_6R_7$, $NR_6R_7$, $NR_5COR_8$, $NR_5CONR_6R_7$, heterocyclyl, heteroaryl, cycloalkyl or aryl,
(c) CN,
(d) $NR_6R_7$,
(e) $CONR_6R_7$,
(f) $NHCONR_6R_7$,
(g) aryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(h) heterocyclyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(i) heteroaryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(j) cycloalkyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(k) cycloalkyl substituted with $C_1$-$C_6$ alkyl wherein $C_1$-$C_6$ alkyl is further substituted with one or more substituents independently selected from $OR_5$, $NR_6R_7$, halogen, CN, or $CONR_6R_7$, or
(l) $OR_8$;

$R_4$ is:
(a) hydrogen,
(b) $C_1$-$C_6$ alkyl optionally substituted with one or more substituents independently selected from halogen, $OR_5$, CN, $COOR_5$, $CONR_6R_7$, $NR_6R_7$, $NR_5COR_8$, heterocyclyl, heteroaryl, cycloalkyl or aryl,
(c) aryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(d) heterocyclyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(e) heteroaryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$, or
(f) cycloalkyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$;
$R_5$ and $R_8$ are each independently:
(a) hydrogen, or
(b) $C_1$-$C_6$ alkyl optionally substituted with one or more substituents independently selected from halogen, CN, $CONR_6R_7$, $NR_6R_7$, heterocyclyl, heteroaryl, cycloalkyl or aryl;
$R_6$ and $R_7$ are each independently:
(a) hydrogen,
(b) $C_1$-$C_6$ alkyl optionally substituted with one or more substituents independently selected from halogen, $OR_5$, CN, $COOR_5$, $CONR_5R_8$, $NR_5R_8$, $NR_5COR_8$, heterocyclyl, heteroaryl, cycloalkyl or aryl,
(c) aryl optionally substituted with one or more substituents independently selected from $C_1$-$C_6$ alkyl, $OR_5$, $NR_5R_8$, halogen, CN, $CONR_5R_8$, $SO_2$-alkyl, $SO_2$-aryl, $OSO_2$-alkyl, $OSO_2$-aryl, or $NHCONR_5R_8$,
(d) heterocyclyl optionally substituted with one or more substituents independently selected from $C_1$-$C_6$ alkyl, $OR_5$, $NR_5R_8$, halogen, CN, $CONR_5R_8$, $SO_2$-alkyl, $SO_2$-aryl, $OSO_2$-alkyl, $OSO_2$-aryl, or $NHCONR_5R_8$,
(e) heteroaryl optionally substituted with one or more substituents independently selected from $C_1$-$C_6$ alkyl, $OR_5$, $NR_5R_8$, halogen, CN, $CONR_5R_8$, $SO_2$-alkyl, $SO_2$-aryl, $OSO_2$-alkyl, $OSO_2$-aryl, or $NHCONR_5R_8$,
(f) cycloalkyl optionally substituted with one or more substituents independently selected from $C_1$-$C_6$ alkyl, $OR_5$, $NR_5R_8$, halogen, CN, $CONR_5R_8$, $SO_2$-alkyl, $SO_2$-aryl, $OSO_2$-alkyl, $OSO_2$-aryl, or $NHCONR_5R_8$, or
(g) $R_6$ and $R_7$ are joined together to form a four to seven member ring.

Typical non-limiting examples of compounds according to the invention include:
(2S,5R)-7-oxo-N-[(2S)-pyrrolidin-2-ylmethyloxy]-6-(sulfooxy)-1,6-diazabicyclo[3.2.1]octane-2-carboxamide;
(2S,5R)-7-oxo-N-[(2R)-pyrrolidin-2-ylmethyloxy]-6-(sulfooxy)-1,6-diazabicyclo[3.2.1]octane-2-carboxamide;
(2S,5R)-7-oxo-N-[(3S)-pyrrolidin-3-ylmethyloxy]-6-(sulfooxy)-1,6-diazabicyclo[3.2.1]octane-2-carboxamide;
(2S,5R)-7-oxo-N-[(3R)-pyrrolidin-3-ylmethyloxy]-6-(sulfooxy)-1,6-diazabicyclo[3.2.1]octane-2-carboxamide;

(2S,5R)—N-{[(2S,4R)-4-hydroxyl-pyrrolidin-2-yl]methyloxy}-7-oxo-6-(sulfooxy)-1,6-diazabicyclo[3.2.1]octane-2-carboxamide;

(2S,5R)—N-{[(2S,4R)-4-cyano-pyrrolidin-2-yl]methyloxy}-7-oxo-6-(sulfooxy)-1,6-diazabicyclo[3.2.1]octane-2-carboxamide;

(2S,5R)—N-{[(5R)-5-cyanopyrrolidin-2-yl]methyloxy}-7-oxo-6-(sulfooxy)-1,6-diazabicyclo[3.2.1]octane-2-carboxamide;

(2S,5R)—N-{[(SR)-5-cyanopyrrolidin-2-yl]methyloxy}-7-oxo-6-(sulfooxy)-1,6-diazabicyclo[3.2.1]octane-2-carboxamide;

(2S,5R)—N-{[(2S,4R)-4-trifluoroacetylamino-pyrrolidin-2-yl]methyloxy}-7-oxo-6-(sulfooxy)-1,6-diazabicyclo[3.2.1]octane-2-carboxamide;

(2S,5R)—N-{[(2S)-1-carbamimidoyl-pyrrolidin-2-yl]methyloxy}-7-oxo-6-(sulfooxy)-1,6-diazabicyclo[3.2.1]octane-2-carboxamide;

(2S,5R)-7-oxo-N-{1-[(2S)-pyrrolidin-2-yl]ethyloxy}-6-(sulfooxy)-1,6-diazabicyclo[3.2.1]octane-2-carboxamide;

(2S,5R)-7-oxo-N-{[(2S)-5-oxopyrrolidin-2-yl]methyloxy}-6-(sulfooxy)-1,6-diazabicyclo[3.2.1]octane-2-carboxamide;

(2S,5R)—N-[(2S)-azetidin-2-ylmethyloxy]-7-oxo-6-(sulfooxy)-1,6-diazabicyclo[3.2.1]octane-2-carboxamide;

(2S,5R)—N-[(2R)-azetidin-2-ylmethyloxy]-7-oxo-6-(sulfooxy)-1,6-diazabicyclo[3.2.1]octane-2-carboxamide;

(2S,5R)-7-oxo-N-(piperidin-4-ylmethyloxy)-6-(sulfooxy)-1,6-diazabicyclo[3.2.1]octane-2-carboxamide;

(2S,5R)-7-oxo-N-((3R,S)-piperidin-3-ylmethyloxy)-6-(sulfooxy)-1,6-diazabicyclo[3.2.1]octane-2-carboxamide;

(2S,5R)-7-oxo-N-((2R,S)piperidin-2-ylmethyloxy)-6-(sulfooxy)-1,6-diazabicyclo[3.2.1]octane-2-carboxamide;

(2S,5R)-7-oxo-N-((2S)piperidin-2-ylmethyloxy)-6-(sulfooxy)-1,6-diazabicyclo[3.2.1]octane-2-carboxamide;

(2S,5R)-7-oxo-N-((2S)piperidin-2-ylmethyloxy)-6-(sulfooxy)-1,6-diazabicyclo[3.2.1]octane-2-carboxamide;

(2S,5R)-7-oxo-N-{1-[(2S)-piperidin-2-yl]ethyloxy}-6-(sulfooxy)-1,6-diazabicyclo[3.2.1]octane-2-carboxamide;

(2S,5R)—N-(azepan-2-ylmethyloxy)-7-oxo-6-(sulfooxy)-1,6-diazabicyclo [3.2.1]octane-2-carboxamide;

(2S)—N-(2,3-dihydro-1H-indol-2-ylmethyloxy)-7-oxo-6-(sulfooxy)-1,6-diazabicyclo[3.2.1]octane-2-carboxamide;

(2S,5R)—N-{[(2R,S)-1,2,3,4-tetrahydro-quinolin-2-yl]methyloxy}-7-oxo-6-(sulfooxy)-1,6-diazabicyclo[3.2.1]octane-2-carboxamide;

(2S,5R)—N-{[(3S)-1,2,3,4-tetrahydro-isquinolin-3-yl]methyloxy}-7-oxo-6-(sulfooxy)-1,6-diazabicyclo[3.2.1]octane-2-carboxamide;

(2S,5R)—N-{[(4S)-1-methyl-1,4,5,6-tetrahydropyrrolol[3,4-c]pyrazol-4-yl]methoxy}-7-oxo-6-(sulfooxy)-1,6-diazabicyclo[3.2.1]octane-2-carboxamide;

(2S,5R)—N-{[(4S)-1H-1,4,5,6-tetrahydropyrrolo[3,4-c]pyrazol-4-yl]methyloxy}-7-oxo-6-(sulfooxy)-1,6-diazabicyclo[3.2.1]octane-2-carboxamide;

(2S)—N-[(4,5-dihydroxy-1,4-dihydropyridin-2-yl)methyloxy]-7-oxo-6-(sulfooxy)-1,6-diazabicyclo[3.2.1]octane-2-carboxamide;

(2S,5R)-7-oxo-N-{[(4S)-2-(2-hydroxyphenyl)-4,5-dihydro-1,3-oxazol-4-yl]methyloxy}-6-(sulfooxy)-1,6-diazabicyclo[3.2.1]octane-2-carboxamide;

(2S,5R)-7-oxo-N-{[(4S)-2-((2S)-pyrrolidin-2-yl)-4,5-dihydro-1,3-oxazol-4-yl]methyloxy}-6-(sulfooxy)-1,6-diazabicyclo[3.2.1]octane-2-carboxamide;

(2S,5R)-7-oxo-N-[(3R,S)-pyrrolidin-3-yloxy]-6-(sulfooxy)-1,6-diazabicyclo[3.2.1]octane-2-carboxamide;

(2S,5R)-7-oxo-N-[(3S)-pyrrolidin-3-yloxy]-6-(sulfooxy)-1,6-diazabicyclo[3.2.1]octane-2-carboxamide;

(2S,5R)-7-oxo-N-[(3R)-pyrrolidin-3-yloxy]-6-(sulfooxy)-1,6-diazabicyclo[3.2.1]octane-2-carboxamide;

(2S,5R)—N-{[(3R,5S)-5-cyanopyrrolidin-3-yl]oxy}-7-oxo-6-(sulfooxy)-1,6-diazabicyclo[3.2.1]octane-2-carboxamide;

(2S,5R)—N-{[(3S,5S)-5-cyanopyrrolidin-3-yl]oxy}-7-oxo-6-(sulfooxy)-1,6-diazabicyclo[3.2.1]octane-2-carboxamide;

(2S,5R)—N-{[(3R,5S)-5-carbamoylpyrrolidin-3-yl]oxy}-7-oxo-6-(sulfooxy)-1,6-diazabicyclo[3.2.1]octane-2-carboxamide;

(2S,5R)—N-(azetidin-3-yloxy)-7-oxo-6-(sulfooxy)-1,6-diazabicyclo[3.2.1]octane-2-carboxamide;

(2S,5R)—N-methyloxy-7-oxo-N-(piperidin-2-ylmethyl)-6-(sulfooxy)-1,6-diazabicyclo[3.2.1]octane-2-carboxamide;

(2S,5R)—N-methyloxy-7-oxo-N-(piperidin-3-ylmethyl)-6-(sulfooxy)-1,6-diazabicyclo[3.2.1]octane-2-carboxamide;

(2S,5R)—N-methyloxy-7-oxo-N-(pyrrolidin-2-ylmethyl)-6-(sulfooxy)-1,6-diazabicyclo[3.2.1]octane-2-carboxamide;

(2S,5R)—N-[(2S)-azetidin-2-ylmethyl]-N-hydroxy-7-oxo-6-(sulfooxy)-1,6-diazabicyclo[3.2.1]octane-2-carboxamide;

(2S,5R)—N-hydroxy-7-oxo-N-[(2S)-pyrrolidin-2-ylmethyl]-6-(sulfooxy)-1,6-diazabicyclo[3.2.1]octane-2-carboxamide;

(2S,5R)—N-hydroxy-7-oxo-N-[(2S)-piperidin-2-ylmethyl]-6-(sulfooxy)-1,6-diazabicyclo[3.2.1]octane-2-carboxamide;

(2S,5R)—N-[(2S)-azepan-2-ylmethyl]-N-hydroxy-7-oxo-6-(sulfooxy)-1,6-diazabicyclo[3.2.1]octane-2-carboxamide;

(2S,5R)—N-[(2R)-azetidin-2-ylmethyl]-N-hydroxy-7-oxo-6-(sulfooxy)-1,6-diazabicyclo[3.2.1]octane-2-carboxamide;

(2S,5R)—N-hydroxy-7-oxo-N-[(2R)-pyrrolidin-2-ylmethyl]-6-(sulfooxy)-1,6-diazabicyclo[3.2.1]octane-2-carboxamide;

(2S,5R)—N-hydroxy-7-oxo-N-[(2R)-piperidin-2-ylmethyl]-6-(sulfooxy)-1,6-diazabicyclo[3.2.1]octane-2-carboxamide;

(2S,5R)—N-[(2R)-azepan-2-ylmethyl]-N-hydroxy-7-oxo-6-(sulfooxy)-1,6-diazabicyclo[3.2.1]octane-2-carboxamide;

or a stereoisomer or a pharmaceutically acceptable salt thereof.

Typical, non-limiting examples of various salt forms of the compounds according to the invention include:

Sodium salt of (2S,5R)—N-[(2S)-azetidin-2-ylmethyl]-N-hydroxy-7-oxo-6-(sulfooxy)-1,6-diazabicyclo[3.2.1]octane-2-carboxamide;

Sodium salt of (2S,5R)—N-hydroxy-7-oxo-N-[(2S)-pyrrolidin-2-ylmethyl]-6-(sulfooxy)-1,6-diazabicyclo[3.2.1]octane-2-carboxamide;

Sodium salt of (2S,5R)—N-hydroxy-7-oxo-N-[(2S)-piperidin-2-ylmethyl]-6-(sulfooxy)-1,6-diazabicyclo[3.2.1]octane-2-carboxamide;

Sodium salt of (2S,5R)—N-[(2S)-azepan-2-ylmethyl]-N-hydroxy-7-oxo-6-(sulfooxy)-1,6-diazabicyclo[3.2.1]octane-2-carboxamide;

Sodium salt of (2S,5R)—N-[(2R)-azetidin-2-ylmethyl]-N-hydroxy-7-oxo-6-(sulfooxy)-1,6-diazabicyclo[3.2.1]octane-2-carboxamide;

Sodium salt of (2S,5R)—N-hydroxy-7-oxo-N-[(2R)-pyrrolidin-2-ylmethyl]-6-(sulfooxy)-1,6-diazabicyclo[3.2.1]octane-2-carboxamide;

Sodium salt of (2S,5R)—N-hydroxy-7-oxo-N-[(2R)-piperidin-2-ylmethyl]-6-(sulfooxy)-1,6-diazabicyclo[3.2.1]octane-2-carboxamide;

Sodium salt of (2S,5R)—N-[(2R)-azepan-2-ylmethyl]-N-hydroxy-7-oxo-6-(sulfooxy)-1,6-diazabicyclo[3.2.1]octane-2-carboxamide;

Sodium salt of (2S,5R)-7-oxo-N-[(2S)-pyrrolidin-2-ylmethyloxy]-6-(sulfooxy)-1,6-diazabicyclo[3.2.1]octane-2-carboxamide;

Sodium salt of (2S,5R)-7-oxo-N-[(2R)-pyrrolidin-2-ylmethyloxy]-6-(sulfooxy)-1,6-diazabicyclo[3.2.1]octane-2-carboxamide;

Sodium salt of (2S,5R)-7-oxo-N-[(3S)-pyrrolidin-3-ylmethyloxy]-6-(sulfooxy)-1,6-diazabicyclo[3.2.1]octane-2-carboxamide;

Sodium salt of (2S,5R)-7-oxo-N-[(3R)-pyrrolidin-3-ylmethyloxy]-6-(sulfooxy)-1,6-diazabicyclo[3.2.1]octane-2-carboxamide;

Sodium salt of (2S,5R)—N-{[(2S,4R)-4-hydroxyl-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4R)-4-cyanol-pyrrolidin-2-yl]methyloxy}-7-oxo-6-(sulfooxy)-1,6-diazabicyclo[3.2.1]octane-2-carboxamide;

Sodium salt of (2S,5R)—N-{[(5R)-5-cyanopyrrolidin-2-yl]methyloxy}-7-oxo-6-(sulfooxy)-1,6-diazabicyclo[3.2.1]octane-2-carboxamide;

Sodium salt of (2S,5R)—N-{[(SR)-5-cyanopyrrolidin-2-yl]methyloxy}-7-oxo-6-(sulfooxy)-1,6-diazabicyclo[3.2.1]octane-2-carboxamide;

Sodium salt of (2S,5R)—N-{[(2S,4R)-4-trifluoroacetylamino-pyrrolidin-2-yl]methyloxy}-7-oxo-6-(sulfooxy)-1,6-diazabicyclo[3.2.1]octane-2-carboxamide;

Sodium salt of (2S,5R)—N-{[(2S)-1-carbamimidoyl-pyrrolidin-2-yl]methyloxy}-7-oxo-6-(sulfooxy)-1,6-diazabicyclo[3.2.1]octane-2-carboxamide;

Sodium salt of (2S,5R)-7-oxo-N-{1-[(2S)-pyrrolidin-2-yl]ethyloxy}-6-(sulfooxy)-1,6-diazabicyclo[3.2.1]octane-2-carboxamide;

Sodium salt of (2S,5R)-7-oxo-N-{[(2S)-5-oxopyrrolidin-2-yl]methyloxy}-6-(sulfooxy)-1,6-diazabicyclo[3.2.1]octane-2-carboxamide;

Sodium salt of (2S,5R)—N-[(2S)-azetidin-2-ylmethyloxy]-7-oxo-6-(sulfooxy)-1,6-diazabicyclo[3.2.1]octane-2-carboxamide;

Sodium salt of (2S,5R)—N-[(2R)-azetidin-2-ylmethyloxy]-7-oxo-6-(sulfooxy)-1,6-diazabicyclo[3.2.1]octane-2-carboxamide;

Sodium salt of (2S,5R)-7-oxo-N-(piperidin-4-ylmethyloxy)-6-(sulfooxy)-1,6-diazabicyclo[3.2.1]octane-2-carboxamide;

Sodium salt of (2S,5R)-7-oxo-N-((3R,S)-piperidin-3-ylmethyloxy)-6-(sulfooxy)-1,6-diazabicyclo[3.2.1]octane-2-carboxamide;

Sodium salt of (2S,5R)-7-oxo-N-((2R,S)piperidin-2-ylmethyloxy)-6-(sulfooxy)-1,6-diazabicyclo[3.2.1]octane-2-carboxamide;

Sodium salt of (2S,5R)-7-oxo-N-((2S)piperidin-2-ylmethyloxy)-6-(sulfooxy)-1,6-diazabicyclo[3.2.1]octane-2-carboxamide;

Sodium salt of (2S,5R)-7-oxo-N-((2S)piperidin-2-ylmethyloxy)-6-(sulfooxy)-1,6-diazabicyclo[3.2.1]octane-2-carboxamide;

Sodium salt of (2S,5R)-7-oxo-N-{1-[(2S)-piperidin-2-yl]ethyloxy}-6-(sulfooxy)-1,6-diazabicyclo[3.2.1]octane-2-carboxamide;

Sodium salt of (2S,5R)—N-(azepan-2-ylmethyloxy)-7-oxo-6-(sulfooxy)-1,6-diazabicyclo[3.2.1]octane-2-carboxamide;

Sodium salt of (2S)—N-(2,3-dihydro-1H-indol-2-ylmethyloxy)-7-oxo-6-(sulfooxy)-1,6-diazabicyclo[3.2.1]octane-2-carboxamide;

Sodium salt of (2S,5R)—N-{[(2R,S)-1,2,3,4-tetrahydroquinolin-2-yl]methyloxy}-7-oxo-6-(sulfooxy)-1,6-diazabicyclo[3.2.1]octane-2-carboxamide;

Sodium salt of (2S,5R)—N-{[(3S)-1,2,3,4-tetrahydro-isquinolin-3-yl]methyloxy}-7-oxo-6-(sulfooxy)-1,6-diazabicyclo[3.2.1]octane-2-carboxamide;

Sodium salt of (2S,5R)—N-{[(4S)-1-methyl-1,4,5,6-tetrahydropyrrolo[3,4-c]pyrazol-4-yl]methoxy}-7-oxo-6-(sulfooxy)-1,6-diazabicyclo[3.2.1]octane-2-carboxamide;

Sodium salt of (2S,5R)—N-{[(4S)-1H-1,4,5,6-tetrahydropyrrolo[3,4-c]pyrazol-4-yl]methyloxy}-7-oxo-6-(sulfooxy)-1,6-diazabicyclo[3.2.1]octane-2-carboxamide;

Sodium salt of (2S)—N-[(4,5-dihydroxy-1,4-dihydropyridin-2-yl)methyloxy]-7-oxo-6-(sulfooxy)-1,6-diazabicyclo[3.2.1]octane-2-carboxamide;

Sodium salt of (2S,5R)-7-oxo-N-{[(4S)-2-(2-hydroxyphenyl)-4,5-dihydro-1,3-oxazol-4-yl]methyloxy}-6-(sulfooxy)-1,6-diazabicyclo[3.2.1]octane-2-carboxamide;

Sodium salt of (2S,5R)-7-oxo-N-{[(4S)-2-((2S)-pyrrolidin-2-yl)-4,5-dihydro-1,3-oxazol-4-yl]methyloxy}-6-(sulfooxy)-1,6-diazabicyclo[3.2.1]octane-2-carboxamide;

Sodium salt of (2S,5R)-7-oxo-N-[(3R,S)-pyrrolidin-3-yloxy]-6-(sulfooxy)-1,6-diazabicyclo[3.2.1]octane-2-carboxamide;

Sodium salt of (2S,5R)-7-oxo-N-[(3S)-pyrrolidin-3-yloxy]-6-(sulfooxy)-1,6-diazabicyclo[3.2.1]octane-2-carboxamide;

Sodium salt of (2S,5R)-7-oxo-N-[(3R)-pyrrolidin-3-yloxy]-6-(sulfooxy)-1,6-diazabicyclo[3.2.1]octane-2-carboxamide;

Sodium salt of (2S,5R)—N-{[(3R,5S)-5-cyanopyrrolidin-3-yl]oxy}-7-oxo-6-(sulfooxy)-1,6-diazabicyclo[3.2.1]octane-2-carboxamide;

Sodium salt of (2S,5R)—N-{[(3S,5S)-5-cyanopyrrolidin-3-yl]oxy}-7-oxo-6-(sulfooxy)-1,6-diazabicyclo[3.2.1]octane-2-carboxamide;

Sodium salt of (2S,5R)—N-{[(3R,5S)-5-carbamoylpyrrolidin-3-yl]oxy}-7-oxo-6-(sulfooxy)-1,6-diazabicyclo[3.2.1]octane-2-carboxamide;

Sodium salt of (2S,5R)—N-(azetidin-3-yloxy)-7-oxo-6-(sulfooxy)-1,6-diazabicyclo[3.2.1]octane-2-carboxamide;

Sodium salt of (2S,5R)—N-methyloxy-7-oxo-N-(piperidin-2-ylmethyl)-6-(sulfooxy)-1,6-diazabicyclo[3.2.1]octane-2-carboxamide;

Sodium salt of (2S,5R)—N-methyloxy-7-oxo-N-(piperidin-3-ylmethyl)-6-(sulfooxy)-1,6-diazabicyclo[3.2.1]octane-2-carboxamide;

Sodium salt of (2S,5R)—N-methyloxy-7-oxo-N-(pyrrolidin-2-ylmethyl)-6-(sulfooxy)-1,6-diazabicyclo[3.2.1]octane-2-carboxamide;

(2S,5R)—N-(2-aminoethyloxy)-7-oxo-6-(sulfooxy)-1,6-diazabicyclo[3.2.1]octane-2-carboxamide trifluoroacetic acid salt;

(2S,5R)—N-(2-carbamimidamidoethyloxy)-7-oxo-6-(sulfooxy)-1,6-diazabicyclo [3.2.1]octane-2-carboxamide trifluoroacetic acid salt;

(2S,5R)—N-(3-aminopropyloxy)-7-oxo-6-(sulfooxy)-1,6-diazabicyclo[3.2.1]octane-2-carboxamide trifluoroacetic acid salt;

(2S,5R)—N-{[(2S)-2,5-diaminopentyl]oxy}-7-oxo-6-(sulfooxy)-1,6-diazabicyclo [3.2.1]octane-2-carboxamide trifluoroaceticacid salt;

(2S,5R)—N-{[(2S,4R)-4-aminopyrrolidin-2-yl]methyloxy}-7-oxo-6-(sulfooxy)-1,6-diazabicyclo[3.2.1]octane-2-carboxamide trifluoroacetic acid salt;

(2S,5R)-7-oxo-N-[(2S)-piperazin-2-ylmethyloxy]-6-(sulfooxy)-1,6-diazabicyclo [3.2.1]octane-2-carboxamide trifluoroaceticacid salt;

(2S,5R)—N-methyloxy-7-oxo-N-(piperazin-2-ylmethyl)-6-(sulfooxy)-1,6-diazabicyclo[3.2.1]octane-2-carboxamide trifluoroaceticacid salt;

Sodium salt of (2S,5R)—N-methoxy-N-methyl-7-oxo-6-(sulfooxy)-1,6-diazabicyclo[3.2.1]octane-2-carboxamide;

Sodium Salt of (2S,5R)—N-methoxy-7-oxo-6-(sulfooxy)-1,6-diazabicyclo[3.2.1]octane-2-carboxamide;

Sodium salt of (2S,5R)—N-hydroxy-N-methyl-7-oxo-6-(sulfooxy)-1,6-diazabicyclo[3.2.1]octane-2-carboxamide;

or a stereoisomer thereof.

In general, the compounds of the invention can be prepared according to the following procedures. A person of skills in the art would appreciate that the described methods can be varied or optimized further to provide the desired and related compounds. In the following procedures, all variables are as defined above.

As described in Scheme-1, trans-6-benzyloxy-7-oxo-1,6-diaza-bicyclo[3.2.1]octane-2-carboxylic acid (1a), which is described PCT International Publication No. WO 2009/091856, was reacted with corresponding substituted hydroxylamines in presence of a suitable coupling agent such as EDC hydrochloride, or dicyclohexylcarbodiimide (DCC) in a suitable solvent such as N,N dimethyl formamide; N,N dimethyl acetamide; 1,4 dioxane; chloroform; dichloromethane; or dichloroethane at a temperature ranging from −15° C. to 60° C. for about 1 to 24 hours to obtain intermediate compound (1b).

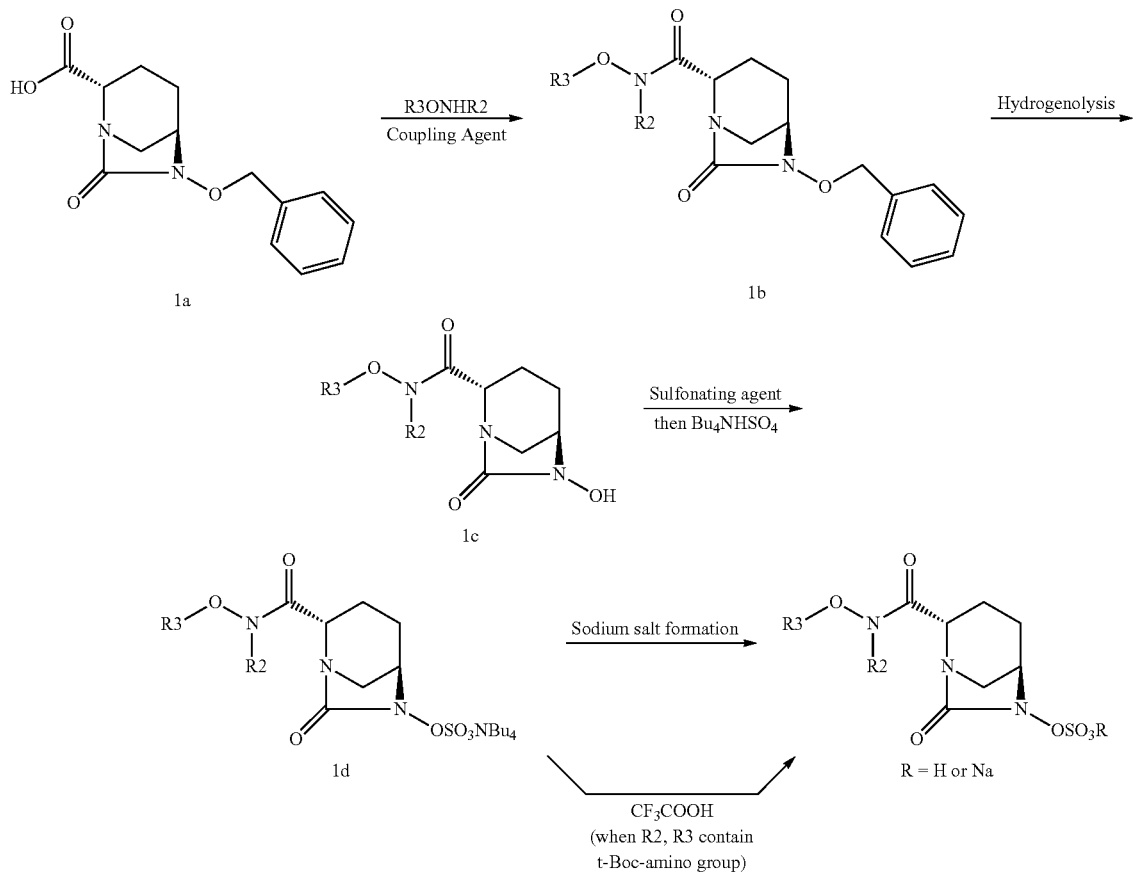

Scheme-1

The intermediate compound (1b) was subjected for hydrogenolysis in presence of a suitable catalyst (e.g. 5% or 10% palladium on carbon, or 20% palladium hydroxide on carbon) in presence of hydrogen source (such as hydrogen gas, ammonium formate, cyclohexene) in a suitable solvent (such as methanol, ethanol, methanol-dichloromethane mix- Sodium salt of (2S,5R)—N-hydroxy-7-oxo-6-(sulfooxy)-1,6-diazabicyclo[3.2.1]octane-2-carboxamide;

Sodium salt of (2S,5R)—N-[(1-methyl-1H-pyrazol-5-yl)methyloxy]-7-oxo-6-(sulfooxy)-1,6-diazabicyclo[3.2.1]octane-2-carboxamide;

ture, or N,N dimethyl formamide-dichloromethane mixture) at a temperature ranging from 25° C. to 60° C. for about 1 to 14 hours to obtain intermediate compound (1c).

The intermediate compound (1c) was sulfonated by reacting it with a sulfonating reagent (such as sulfur trioxide-pyridine complex, or sulfur trioxide-N,N-dimethyl formamide complex) in a suitable solvent (such as pyridine, N,N-dimethyl formamide) at a temperature ranging from about 25° C. to 90° C. for about 1 to 24 hours to obtain pyridine salt of sulfonic acid which when treated with tetrabutyl ammonium sulfate provided terabutylammonium salt of sulfonic acid as an intermediate compound (1d).

Some compounds according to the invention were isolated as zwitterions, by treating intermediate compound (1d) with trifluoroacetic acid, in a suitable solvent (such as dichloromethane, chloroform, acetonitrile) at a temperature ranging from –10° C. to 40° C. for about 1 to 14 hours, especially when R in intermediate compound (1d) contained tert-butoxycarbonyl protected amine function.

Some other compounds according to the invention were isolated as a sodium salt, by passing a solution of intermediate compound (1d) through a column of sodium form of Amberlite 200C resin in mixture of tetrahydrofuran-water followed by evaporation of the solvent under vacuum.

The required substituted hydroxyl amines were prepared as shown in Scheme-2 as described in Synthesis 682-4 (1976) and U.S. Pat. No. 5,120,849 (1992)

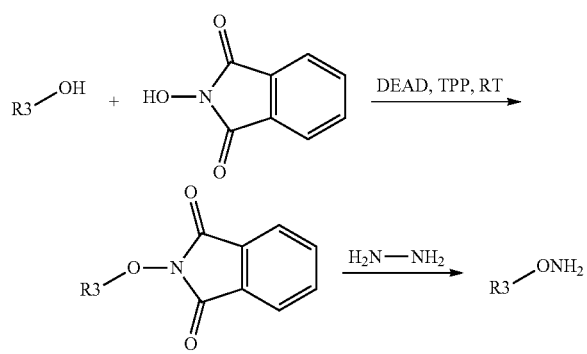

In some embodiments, there are provided pharmaceutical compositions comprising a compound of Formula (I), or a stereoisomer or a pharmaceutically acceptable salt thereof.

In some other embodiments, there is provided a method for preventing or treating bacterial infection in a subject, said method comprising administering to said subject a pharmaceutically effective amount of a compound of Formula (I) or a stereoisomer or a pharmaceutically acceptable salt thereof.

In some embodiments, there is provided a method for preventing or treating a bacterial infection in a subject, said infection being caused by bacteria producing one or more beta-lactamase enzymes, wherein the method comprises administering to said subject a pharmaceutically effective amount of a compound of Formula (I) or a stereoisomer or a pharmaceutically acceptable salt thereof.

In some other embodiments, there is provided a method for preventing or treating bacterial infection in a subject, said method comprising administering to said subject a pharmaceutically effective amount of a pharmaceutical composition comprising a compound of Formula (I) or a stereoisomer or a pharmaceutically acceptable salt thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising a compound of Formula (I) or a stereoisomer or a pharmaceutically acceptable salt thereof.

In some embodiments, there are provided pharmaceutical compositions comprising: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In some other embodiments, there are provided pharmaceutical compositions comprising: (a) a compound of Formula (I), or a stereoisomer or a pharmaceutically acceptable salt thereof, and (b) at least one antibacterial agent or a pharmaceutically acceptable derivative thereof.

In some other embodiments, there are provided pharmaceutical compositions comprising: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In some other embodiments, there is provided a method for preventing or treating bacterial infection in a subject, said method comprising administering to said subject a pharmaceutically effective amount of a pharmaceutical composition comprising: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In some other embodiments, there is provided a method for preventing or treating bacterial infection in a subject, said method comprising administering to said subject a pharmaceutically effective amount of a pharmaceutical composition comprising: (a) a compound of Formula (I), or a stereoisomer or a pharmaceutically acceptable salt thereof, and (b) at least one antibacterial agent or a pharmaceutically acceptable derivative thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising: (a) a compound of Formula (I), or a stereoisomer or a pharmaceutically acceptable salt thereof, and (b) at least one antibacterial agent or a pharmaceutically acceptable derivative thereof.

In some other embodiments, there is provided a method for preventing or treating a bacterial infection in a subject, said method comprising administering to said subject a pharmaceutically effective amount of a pharmaceutical composition comprising: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In some other embodiments, there is provided a method for preventing or treating bacterial infection in a subject, said method comprising administering to said subject a pharmaceutically effective amount of: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In some other embodiments, there is provided a method for preventing or treating bacterial infection in a subject, said method comprising administering to said subject a pharmaceutically effective amount of: (a) a compound of Formula (I), or a stereoisomer or a pharmaceutically acceptable salt thereof, and (b) at least one antibacterial agent or a pharmaceutically acceptable derivative thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of: (a) a compound of Formula (I), or a stereoisomer or a pharmaceutically acceptable salt thereof, and (b) at least one antibacterial agent or a pharmaceutically acceptable derivative thereof.

In some other embodiments, there is provided a method for preventing or treating bacterial infection in a subject, said method comprising administering to said subject a pharmaceutically effective amount of: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In some embodiments, there are provided methods for increasing antibacterial effectiveness of a antibacterial agent in a subject, said method comprising co-administering said antibacterial agent or a pharmaceutically acceptable derivative thereof with a pharmaceutically effective amount of a compound of Formula (I) or a stereoisomer or a pharmaceutically acceptable salt thereof.

In some embodiments, the compositions and methods according to the invention use compounds of Formula (I) or a stereoisomer or a pharmaceutically acceptable salt thereof in combination with at least one antibacterial agent or a pharmaceutically acceptable derivative thereof. A wide variety of antibacterial agents can be used. Typical, non-limiting examples of antibacterial agents include one or more of antibacterial compounds generally classified as aminoglycosides, Ansamycins, Carbacephems, Cephalosporins, Cephamycins, Lincosamides, Lipopeptides, Macrolides, Monobactams, Nitrofurans, Penicillins, Polypeptides, Quinolones, Sulfonamides, Tetracyclines, Oxazolidinone and the like.

Typical, non-limiting examples of Aminoglycoside antibacterial agents include Amikacin, Gentamicin, Kanamycin, Neomycin, Netilmicin, Tobramycin, Paromomycin, Arbekacin, Streptomycin, Apramycin and the like.

Typical, non-limiting examples of Ansamycin antibacterial agents include Geldanamycin, Herbimycin and the like.

Typical, non-limiting examples of Carbacephem antibacterial agents include Loracarbef and the like.

Typical, non-limiting examples of Carbapenem antibacterial agents include Ertapenem, Doripenem, Imipenem, Meropenem and the like.

Typical, non-limiting examples of Cephalosporin and Cephamycin antibacterial agents include Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cephamycin, Cefoxitin, Cefotetan, Cefmetazole, Carbacephem, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Oxacephem, Cefepime, Cefozopran, Cefpirome, Cefquinome, Ceftobiprole, Ceftiofur, Cefquinome, Cefovecin, CXA-101, Ceftaroline, Ceftobiprole etc.

Typical, non-limiting examples of Lincosamide antibacterial agents include Clindamycin, Lincomycin and the like.

Typical, non-limiting examples of Macrolide antibacterial agents include Azithromycin, Clarithromycin, Dirithromycin, Erythromycin, Roxithromycin, Troleandomycin, Telithromycin, Spectinomycin, Solithromycin and the like.

Typical, non-limiting examples of Monobactam antibacterial agents include Aztreonam and the like.

Typical, non-limiting examples of Nitrofuran antibacterial agents include Furazolidone, Nitrofurantoin and the like.

Typical, non-limiting examples of Penicillin antibacterial agents include Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin, Ticarcillin and the like.

Typical, non-limiting examples of Polypeptide antibacterial agents include Bacitracin, Colistin, Polymyxin B and the like.

Typical, non-limiting examples of Quinolone antibacterial agents include Ciprofloxacin, Enoxacin, Gatifloxacin, Levofloxacin, Lomefloxacin, Moxifloxacin, Nalidixic acid, Levonadifloxacin, Norfloxacin, Ofloxacin, Trovafloxacin, Grepafloxacin, Sparfloxacin, Temafloxacin and the like.

Typical, non-limiting examples of Sulfonamide antibacterial agents include Mafenide, Sulfonamidochrysoidine, Sulfacetamide, Sulfadiazine, Sulfamethizole, Sulfamethoxazole, Sulfasalazine, Sulfisoxazole, Trimethoprim and the like.

Typical, non-limiting examples of Tetracycline antibacterial agents include Demeclocycline, Doxycycline, Minocycline, Oxytetracycline, Tetracycline, Tigecycline and the like.

Typical, non-limiting examples of Oxazolidinone antibacterial agents include Tedizolid, Linezolid, Ranbezolid, Torezolid, Radezolid etc.

The pharmaceutical compositions according to the invention may include one or more pharmaceutically acceptable carriers or excipients or the like, Typical, non-limiting examples of such carriers or excipient include mannitol, lactose, starch, magnesium stearate, sodium saccharine, talcum, cellulose, sodium crosscarmellose, glucose, gelatin, sucrose, magnesium carbonate, wetting agents, emulsifying agents, solubilizing agents, pH buffering agents, lubricants, stabilizing agents, binding agents etc.

The pharmaceutical compositions according to this invention can exist in various forms. In some embodiments, the pharmaceutical composition is in the form of a powder or a solution. In some other embodiments, the pharmaceutical compositions according to the invention are in the form of a powder that can be reconstituted by addition of a compatible reconstitution diluent prior to parenteral administration. Non-limiting example of such a compatible reconstitution diluent includes water.

In some other embodiments, the pharmaceutical compositions according to the invention are in the form of a frozen composition that can be diluted with a compatible diluent prior to parenteral administration.

In some other embodiments, the pharmaceutical compositions according to the invention are in the form ready to use for parenteral administration.

In the methods according to the invention, the pharmaceutical composition and/or other pharmaceutically active ingredients disclosed herein may be administered by any appropriate method, which serves to deliver the composition or its constituents or the active ingredients to the desired site. The method of administration can vary depending on various factors, such as for example, the components of the pharmaceutical composition and nature of the active ingredients, the site of the potential or actual infection, the microorganism (e.g. bacteria) involved, severity of infection, age and physical condition of the subject. Some non-limiting examples of administering the composition to a subject according to this invention include oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash.

The compositions according to the invention can be formulated into various dosage forms wherein the active ingredients and/or excipients may be present either together (e.g. as an admixture) or as separate components. When the various ingredients in the composition are formulated as a mixture, such composition can be delivered by administering such a mixture. The composition or dosage form wherein the ingredients do not come as a mixture, but come as separate components, such composition/dosage form may be administered in several ways. In one possible way, the ingredients may be mixed in the desired proportions and the mixture is then administered as required. Alternatively, the components or the ingredients (active or inert) may be separately administered (simultaneously or one after the other) in appropriate proportion so as to achieve the same or equivalent therapeutic level or effect as would have been achieved by administration of the equivalent mixture.

Similarly, in the methods according to the invention, the active ingredients disclosed herein may be administered to a subject in several ways depending on the requirements. In some embodiments, the active ingredients are admixed in appropriate amounts and then the admixture is administered to a subject. In some other embodiments, the active ingredients are administered separately. Since the invention contemplates that the active ingredients agents may be administered separately, the invention further provides for combining separate pharmaceutical compositions in kit form. The kit may comprise one or more separate pharmaceutical compositions, each comprising one or more active ingredients. Each of such separate compositions may be present in a separate container such as a bottle, vial, syringes, boxes, bags, and the like. Typically, the kit comprises directions for the administration of the separate components. The kit form is particularly advantageous when the separate components are preferably administered in different dosage forms (e.g., oral and parenteral) or are administered at different dosage intervals. When the active ingredients are administered separately, they may be administered simultaneously or sequentially.

The pharmaceutical composition or the active ingredients according to the present invention may be formulated into a variety of dosage forms. Typical, non-limiting examples of dosage forms include solid, semi-solid, liquid and aerosol dosage forms; such as tablets, capsules, powders, solutions, suspensions, suppositories, aerosols, granules, emulsions, syrups, elixirs and a like.

In general, the pharmaceutical compositions and method disclosed herein are useful in preventing or treating bacterial infections. Advantageously, the compositions and methods disclosed herein are also effective in preventing or treating infections caused by bacteria that are considered to be less or not susceptible to one or more of known antibacterial agents or their known compositions. Some non-limiting examples of such bacteria known to have developed resistance to various antibacterial agents include *Acinetobacter, E. coli, Pseudomonas aeruginosa, Staphylococcus aureus, Enterobacter, Klebsiella, Citrobacter* and a like. Other non-limiting examples of infections that may be prevented or treated using the compositions and/or methods of the invention include: skin and soft tissue infections, febrile neutropenia, urinary tract infection, intraabdominal infections, respiratory tract infections, pneumonia (nosocomial), bacteremia meningitis, surgical, infections etc.

Surprisingly, the compounds, compositions and methods according to the invention are also effective in preventing or treating bacterial infections that are caused by bacteria producing one or more beta-lactamase enzymes. The ability of compositions and methods according to the present invention to treat such resistant bacteria with typical beta-lactam antibiotics represents a significant improvement in the art.

In general, the compounds of Formula (I) or a stereoisomer or pharmaceutically acceptable salt thereof according to invention are also useful in increasing antibacterial effectiveness of a antibacterial agent in a subject. The antibacterial effectiveness of one or more antibacterial agents may increased, for example, by co-administering said antibacterial agent or a pharmaceutically acceptable salt thereof with a pharmaceutically effective amount of a compound of Formula (I) or a stereoisomer or a pharmaceutically acceptable salt thereof according to the invention.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example-1

(2S,5R)-7-oxo-N-[(2S)-pyrrolidin-2-ylmethyloxy]-6-(sulfooxy)-1,6-diazabicyclo[3.2.1]octane-2-carboxamide

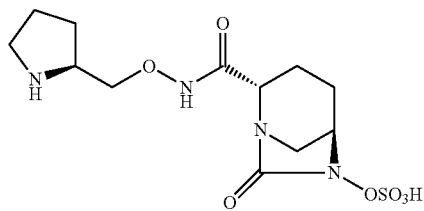

Preparation of Side Chain: tert-butyl (2S)-2-[(aminooxy)methyl]pyrrolidine-1 carboxylate

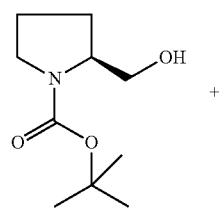
+

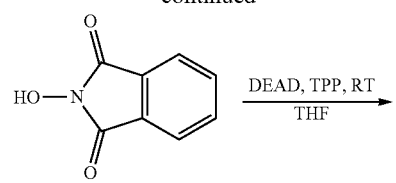

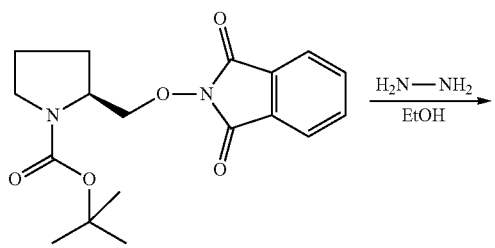

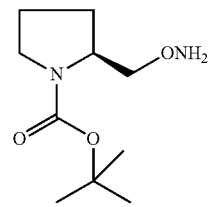

Step-1

A solution of DEAD (17.14 ml, 1.092 mol) in THF (366 ml) was cooled to −10° C. and to this was added slowly a solution of TPP (22.49 gm, 1.092 mmol) in THF (36 ml). After stirring for 45 minutes below −10° C., a solution of tert-butyl (2S)-2-(hydroxymethyl) pyrrolidine-1-carboxylate (12.2 gm, 0.606 mol) in THF (36 ml) was added and after stirring for 5 minutes a solution of N-Hydroxy phthalimide (9.88 gm, 0.606 mol) in THF (122 ml) was added. The resulting mixture was allowed to warm to RT and stirring continued further. After 16 hours, the solvent was evaporated under reduced pressure and the residue diluted with ethyl acetate (250 ml) and the ethyl acetate layer washed with sat. aqueous sodium bicarbonate solution (1×122 ml), water (1×122 ml) and Brine (1×61 ml). The solvent was evaporated under reduced pressure and the residue was purified by column chromatography, over silica gel. Elution with 12% Acetone in hexane and the concentration of the combined fractions gave the product as pale yellow oil, 20.6 gm, in 98% yield.

Analysis:

Mass: 347.3 (M+H) for MW-346.39 and M.F- $C_{18}H_{22}N_2O_5$

Step-II:

To a solution of the Phthalimide (4 gm, 0.115 mol) in ethanol (60 ml) and was added hydrazine hydrate (0.84 ml, 0.173 mol) at RT. After stirring for 1 hour the insolubles were separated by filtration. The filtrate was concentrated under reduced pressure and the residue was diluted with DCM (40 ml). The DCM layer was washed with water (2×40 ml) and brine (1×40 ml). The solvent was evaporated under reduced pressure to obtain 2.4 gm residue. This was used as such for the next coupling reaction.

Coupling Reaction

Step-1: Preparation of (2S,5R)-2-[(6-benzyloxy-7-oxo-1,6-diaza-bicyclo[3.2.1]octane-2-carbonyl)-methyloxycarbamoyl]-(2S)-pyrrolidine-1-carboxylic acid tert-butyl ester

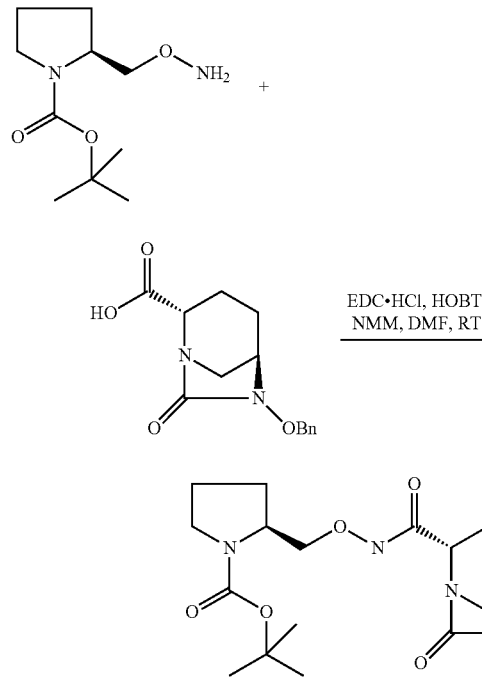

Step-2: Preparation of Tetrabutylammonium Salt of (2S,5R)-2-[(6-sulfooxy-7-oxo-1,6-diaza-bicyclo[3.2.1]octane-2-carbonyl)-methyloxycarbamoyl]-(2S)-pyrrolidine-1-carboxylic acid tert-butyl ester

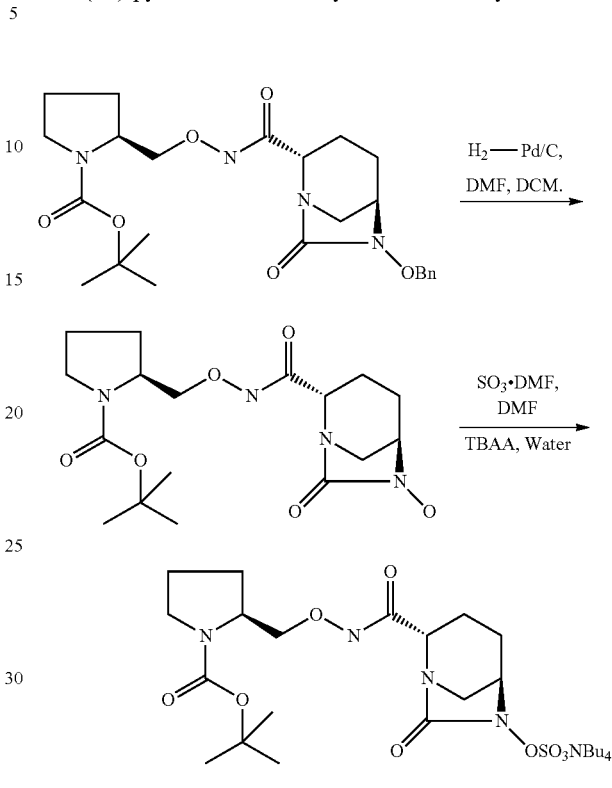

To a clear solution of (2S,5R)-6-(benzyloxy)-7-oxo-1,6-diazabicyclo[3.2.1]octane-2-carboxylic acid (3.06 gm, 0.111 mol) in N,N-dimethyl formamide (24 ml), was added HOBt (1.49 gm, 0.111 mol) followed by EDC hydrochloride (3.18 gm, 0.166 mol) and NMM (3.39, 0.333 mol) at about 25° C. to 35° C. under stirring. The reaction mixture was stirred for 15 minutes and a solution of 2-Aminooxymethyl-(S)-pyrrolidine-1-carboxylic acid t-butyl ester (2.4 gm, 0.100 mol) dissolved in N,N-dimethyl formamide (15 ml). The reaction mixture was stirred at a temperature between 25° C. to 35° C. for 16 hours and the resulting mixture was poured into water (120 ml) and mixture extracted with Ethyl acetate (3×25 ml). The ethyl acetate layer was washed with water (1×100 ml) and brine (1×50 ml). The solvent was evaporated under reduced pressure and the residue was purified by column chromatography over silica gel. Elution with 10% acetone in hexane and concentration of the combined fractions gave the product as a white solid, 2.1 gm, 64% yield.

Analysis:

Mass: 475.4 (M+H) for MW-474.56 and M.F-$C_{24}H_{34}N_4O_6$ $^1$H NMR: Solvent (CDCl$_3$): 10.16 (s, 1H), 7.43-7.35 (m, 5H), 5.06-4.88 (dd, 2H), 4.12 (s, 1H), 3.94-0.393 (d, 2H), 3.83 (unresolved s, 1H), 3.75-3.73 (m, 1H), 3.37-3.28 (dt, 2H), 3.02-2.86 (dd, 2H), 2.29-2.25 (m, 1H), 1.99-1.82 (m, 5H), 1.75-1.61 (m, 2H), 1.45 (s, 9H).

A solution of the Benzyl compound (2.1 g, mmol) in 1:1 mixture of DMF:DCM (5 ml), was hydrogenated over 10% Pd/C (125 mg) over 1 atmosphere of Hydrogen balloon. After stirring for 4 hours the reaction mixture was filtered over celite. The filtrate was concentrated under reduced pressure and the residue obtained was dissolved in fresh DMF (2.5 ml) and cooled to 10° C.SO$_3$.DMF complex (193 mg, 12.6 mmol) was added and the reaction mixture was allowed to warm to RT. After stirring RM at RT for 1.5 hours, TBAA (379 mg, 12.6 mmol) in water (1.25 ml) was added to the reaction mixture and stirring continued further for 2 hours. The volatiles were removed by high vacuum distillation and the residue co-evaporated with xylene (2×25 ml) to remove traces of DMF. The residue obtained was diluted with water (20 ml) and extracted with DCM (3×20 ml). The combined DCM layer was washed with water (2×20 ml). The DCM layer was dried and the solvent evaporated under reduced pressure. The crude residue was triturated with Diethyl ether (3×25 ml) to obtain the product as a white solid, 610 mg, 82% yield.

Analysis:

Mass: 463.4 (M–H) for MW-705.96 and M.F-$C_{33}H_{63}N_5O_9$ S.

$^1$H NMR: Solvent (CDCl$_3$): 10.2 (s, 1H), 4.35 (s, 1H), 4.14 (s, 1H), 3.91-3.92 (d, 2H), 3.74 (m, 1H), 3.36-3.27 (m, 10H), 2.96-2.88 (dd, 2H), 2.31-2.26 (m, 2H), 2.19-1.98 (m, 2H), 1.95-1.70 (m, 4H), 1.68-1.62 (p, 8H), 1.49-1.40 (m, 17H), 1.02-0.98 (t, 12H).

Step-3: Preparation of (2S,5R)-7-oxo-N-[(2S)-pyrrolidin-2-ylmethyloxy]-6-(sulfooxy)-1,6-diazabicyclo[3.2.1]octane-2-carboxamide

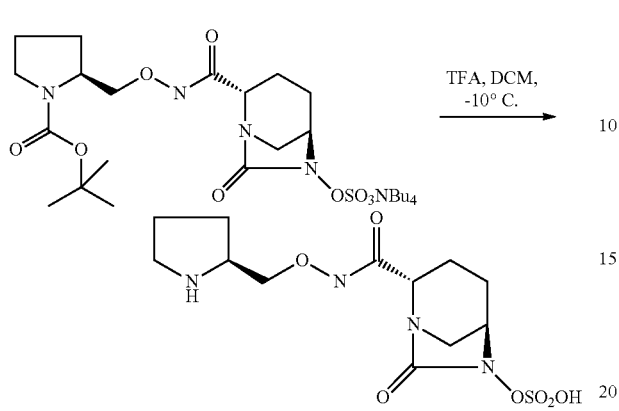

To a cooled (−10° C.) solution of TBA compound (300 mg, 4.2 mmol) in DCM (2.5 ml) was added TFA (2.5 ml). After stirring for 30 min. at −10° C. the solvent was evaporated under reduced pressure. The residue obtained was triturated with diethyl ether to obtain white solid. The solid was washed with diethyl ether (3×25 ml), Acetonitrile (2×25 ml) and DCM (2×25 ml). And the residual solid dried under reduced pressure (4 mmHg), to obtain the product as a white solid 140 mg, 91% yield.

Analysis:
Mass: 363.2 (M−H) for MW- 364.37 and M.F- $C_{12}H_{20}N_4O_7S$.
$^1$H NMR: Solvent (DMSO-D6): 11.73 (s, 1H), 8.62-8.83 (d, 2H), 3.88-4.00 (m, 3H), 3.74-3.81 (m, 2H), 3.19 (t, 2H), 2.94-3.04 (dd, 2H), 1.96-2.03 (m, 2H), 1.80-1.92 (m, 3H), 1.54-1.73 (m, 3H).

Examples 2 to 39 (Table 1) were prepared using the procedure described as in Example-1 and using corresponding $R_1CH_2ONH_2$, in place of 2-Aminooxymethyl-(S)-pyrrolidine-1-carboxylic acid t-butyl ester. These compounds were isolated as zwitterions.

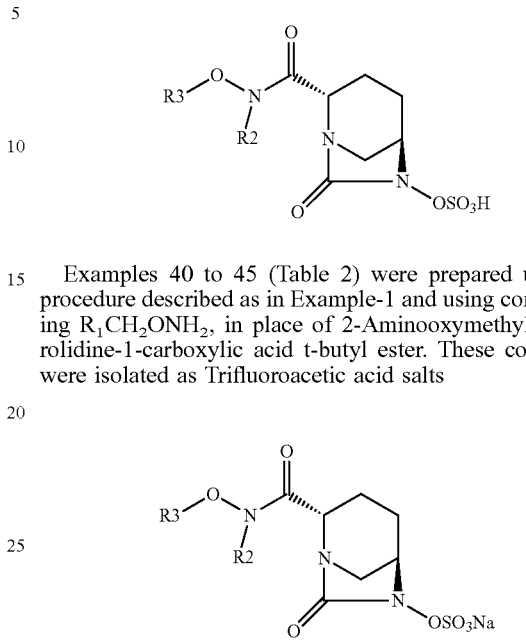

Examples 40 to 45 (Table 2) were prepared using the procedure described as in Example-1 and using corresponding $R_1CH_2ONH_2$, in place of 2-Aminooxymethyl-(S)-pyrrolidine-1-carboxylic acid t-butyl ester. These compounds were isolated as Trifluoroacetic acid salts Examples 46 to 50 (Table 3) were prepared using the procedure described as in Example-1 and using corresponding $R_1CH_2ONH_2$, in place of 2-Aminooxymethyl-(S)-pyrrolidine-1-carboxylic acid t-butyl ester. These compounds were isolated as sodium salts.

Procedure: A solution of intermediate sulphate compound (1d) was passed through a column of sodium form of Amberlite 200C resin in mixture of tetrahydrofuran-water followed by evaporation of the solvent from the combined fractions under reduced pressure (4 mmHg).

TABLE 1

| Example No. | R1 | R2 | R3 | $^1$H-NMR (DMSO-$d_6$)/$D_2$O, δ values | Mass (ES-1) as free acid (MF) |
|---|---|---|---|---|---|
| 1. | SO$_2$OH | H | (pyrrolidinyl structure) | (DMSO-$d_6$): δ 11.73 (s, 1H), 8.62-8.83 (d, 2H), 3.88-4.00 (m, 3H), 3.74-3.81 (m, 2H), 3.19 (t, 2H), 2.94-3.04 (dd, 2H), 1.96-2.03 (m, 2H), 1.80-1.92 (m, 3H), 1.54-1.73 (m, 3H). | 363.1 ($C_{12}H_{20}N_4O_7S$) |
| 2. | SO$_2$OH | H | (pyrrolidinyl structure) | (DMSO-$d_6$): δ 11.72 (br s, 1H), 8.88 (br s, 1H), 8.60 (br s, 1H), 3.88-4.04 (m, 3H), 3.72-3.84 (m, 2H), 2.96-3.28 (m, 4H), 1.52-2.10 (s, 8H). | 363.1 (M − 1) $C_{12}H_{20}N_4O_7S$ |
| 3. | SO$_2$OH | H | (pyrrolidinyl structure) | (DMSO-$d_6$): δ 11.50 (br s, 1H), 8.60 (br s, 2H), 3.98-4.02 (m, 1H), 3.68-3.82 (m, 3H), 3.30-3.40 (m, 1H), 2.96-3.26 (m, 5H), 2.54-2.60 (m, 1H), 1.94-2.08 (m, 2H), 1.84-1.88 (m, 1H), 1.64-1.78 (s, 3H). | 363.1 (M − 1) $C_{12}H_{20}N_4O_7S$ |
| 4. | SO$_2$OH | H | (pyrrolidinyl structure) | (DMSO-$d_6$): δ 11.50 (br s, 1H), 8.60 (br s, 2H), 3.98-4.02 (m, 1H), 3.69-3.84 (m, 3H), 2.96-3.36 (m, 6H), 2.54-2.60 (m, 1H), 1.94-2.08 (m, 2H), 1.82-1.90 (m, 1H), 1.60-1.72 (s, 3H). | 363.1 (M − 1) $C_{12}H_{20}N_4O_7S$ |

TABLE 1-continued

| Example No. | R1 | R2 | R3 | $^1$H-NMR (DMSO-d$_6$)/D$_2$O, δ values | Mass (ES-1) as free acid (MF) |
|---|---|---|---|---|---|
| 5. | SO$_2$OH | H | 4-hydroxypyrrolidin-2-yl (structure) | — | 379.1 (C$_{12}$H$_{20}$N$_4$O$_8$S) |
| 6. | SO$_2$OH | H | 4-cyanopyrrolidin-2-yl (structure) | — | 388.1 (C$_{13}$H$_{19}$N$_5$O$_7$S) |
| 7. | SO$_2$OH | H | 5-cyanopyrrolidin-2-yl (structure) | — | 388.1 (C$_{13}$H$_{19}$N$_5$O$_7$S) |
| 8. | SO$_2$OH | H | 5-cyanopyrrolidin-2-yl (stereoisomer, structure) | — | 388.1 (C$_{13}$H$_{19}$N$_5$O$_7$S) |
| 9. | SO$_2$OH | H | 4-(trifluoroacetamido)pyrrolidin-2-yl (structure) | (DMSO-d$_6$): δ 11.6 (s, 1H), 9.75 (d, 1H), 8.91-9.21(br, 2H), 4.40-4.46 (q, 1H), 4.02(s, 2H), 3.86(bs, 1H), 3.52-3.79 (d, 1H), 3.47-3.49 (t, 1H), 3.12-3.19 (m, 2H), 3.02-3.052(d, 1H), 2.94-2.96 (d, 1H), 2.38-2.45(m, 1H) 2.003-2.054(m, 1H), 1.87-1.89(m, 1H), 1.58-1.74(m, 2H), 1.54-1.58(m, 2H). | [ES−] 473.9 [ES+] 476.0 (C$_{14}$H$_{20}$N$_5$O$_8$SF$_3$) |
| 10. | SO$_2$OH | H | 2-guanidinopyrrolidin-1-yl (structure) | (DMSO-d$_6$) δ: 10.9 (s, 1H), 7.65 (d, 3H), 4.23 (s, 1H), 4.403 (m, 2H), 3.87-3.92 (m, 2H), 3.70-3.74 (dd, 1H), 3.47-3.50 (m, 1H), 2.91-3.02 (dd, 2H), 1.83-1.89 (m, 6H), 1.65-1.67(m, 2H). | 405.15 (C$_{13}$H$_{22}$N$_6$O$_7$S) |
| 11. | SO$_2$OH | H | 2-(propan-2-yl)pyrrolidin-2-yl (structure) | (DMSO-d$_6$): 12.04 (bs, 1H), 8.42-9.20 (bs, 2H), 4.09 (bs, 1H), 4.01 (s, 1H), 3.83 (m, 1H), 3.67 (m, 1H), 3.21 (m, 2H), 2.92-3.03 (m, 2H), 1.69-2.05δ (m, 8H), 1.23-1.24 (d, 3H), | [ES−] 377.0, [ES+] 379.0 (C$_{13}$H$_{22}$N$_4$O$_7$S) |
| 12. | SO$_2$OH | H | 5-oxopyrrolidin-2-yl (structure) | – | 377.1 (C$_{12}$H$_{18}$N$_4$O$_8$S) |
| 13. | SO$_2$OH | H | azetidin-2-yl (structure) | – | 350.1(M + 1) (C$_{11}$H$_{18}$N$_4$O$_7$S) |
| 14. | SO$_2$OH | H | azetidin-2-yl (stereoisomer, structure) | – | 350.1(M + 1) (C$_{11}$H$_{18}$N$_4$O$_7$S) |
| 15. | SO$_2$OH | H | piperidin-4-yl (structure) | (DMSO-d$_6$) δ 11.37 (s, 1H), 8.39 (bs, 1H), 8.1 (bs, 1H), 3.98 (s, 1H), 3.67-3.68 (d, 2H), 3.64-3.69(d, 2H), 3.24-3.27 (d, 2H), 3.07-3.12 (m, 1H), 2.99 (s, 2H), 2.8-2.89 (m, 2H), 1.85-1.96 (m, 4H), 1.65-1.67 (m, 2H), 1.55 (m, 1H), 1.28-1.36 (m, 2H). | [ES−] 377.2 [ES+] 379.1 (C$_{13}$H$_{23}$N$_4$O$_7$S) |

TABLE 1-continued

| Example No. | R1 | R2 | R3 | ¹H-NMR (DMSO-d₆)/D₂O, δ values | Mass (ES-1) as free acid (MF) |
|---|---|---|---|---|---|
| 16. | SO₂OH | H | piperidine (NH), 3-substituted | (DMSO-d₆): δ 11.43 (s, 1H), 8.48-8.50 (d, 1H), 8.24-8.27 (d, 1H), 3.99 (s, 1H), 3.61-3.73 (m, 3H), 3.34-3.37 (m, 2H), 3.16-3.21 (m, 2H), 2.99 (s, 2H), 2.68-2.77 (m, 3H), 1.85-2.00 (m, 4H), 1.65-1.79 (m, 4H), 1.53-1.58 (m, 2H), 1.20-1.30 (m, 2H). | 378.40 (C₁₃H₂₂N₄O₇S) |
| 17. | SO₂OH | H | piperidine (NH), 2-substituted | (DMSO-d₆): δ 11.85 (br s, 1H), 11.77 (br s, 1H), 8.47 (br s, 1H), 4.00-4.04 (m, 1H), 3.80-3.95 (m, 3H), 2.76-3.18 (m, 4H), 1.98-2.06 (m, 1H), 1.84-1.94 (m, 1H), 1.62-1.80 (m, 5H), 1.28-1.60 (m, 4H). | 377.2 (M − 1) (C₁₃H₂₂N₄O₇S) |
| 18. | SO₂OH | H | piperidine (NH), 2-substituted | (DMSO-d₆): δ 11.78 (s, 1H), 8.36-8.60 (m, 2H), 3.76-4.06 (m, 4H), 2.70-3.06 (m, 4H), 1.98-2.04 (m, 1H), 1.84-1.92 (m, 1H), 1.62-1.80 (m, 5H), 1.28-1.60 (m, 4H). | 377.0 (M − 1) (C₁₃H₂₂N₄O₇S) |
| 19. | SO₂OH | H | piperidine (NH), 2-substituted | (DMSO-d₆): δ 11.90 (s, 1H), 8.40-8.60 (m, 2H), 3.76-4.06 (m, 4H), 2.70-3.06 (m, 4H), 1.98-2.04 (m, 2H), 1.84-1.92 (m, 1H), 1.62-1.80 (m, 5H), 1.28-1.60 (m, 4H). | 379.0 (M + 1) (C₁₃H₂₂N₄O₇S) |
| 20. | SO₂OH | H | piperidine (NH), 2-isopropyl | (DMSO-d₆): δ 11.78 (s, 1H), 8.16-8.60 (m, 2H), 3.98-4.03 (m, 3H), 3.78-3.80 (d, 1H), 3.23-3.28 (m, 4H), 2.85-3.06 (m, 4H), 1.94-2.05 (m, 2H), 1.57-1.87 (m, 8H), 1.30-1.49 (m, 3H), 1.15-1.24 (m, 4H). | 391.0 (M − 1) (C₁₄H₂₄N₄O₇S) |
| 21. | SO₂OH | H | azepane (NH), 2-substituted | — | 391.2 (M − 1) (C₁₄H₂₄N₄O₇S) |
| 22. | SO₂OH | H | indoline, 2-substituted | (DMSO-d₆) D₂O exhange): δ 11.5 (M, 1H), 7.128-7.012 (m, 2H), 6.76 (m, 2H), 4.12 (m, 1H) 3.98 (s, 1H), 3.90-3.73 (m, 3H), 3.14-3.08 (dd, 2H), 2.99 (d, 2H), 2.78-2.72 (m, 1H) 2.00-1.98 (m, 1H), 1.85 (m, 1H), 1.71-1.66 (m, 2H). | 411.3 (M − 1) 413.3 (M + 1) (C₁₆H₂₀N₄O₇S) |
| 23. | SO₂OH | H | 1,2,3,4-tetrahydroquinoline, 2-substituted | (DMSO-d₆, D₂O exchange): δ 6.96-6.99 (m, 2H), 6.68-6.73 (m, 2H), 3.98 (d, 1H), 3.90 (dd, 1H) 3.72-3.77 (m, 2H), 3.45-3.55 (m, 1H), 3.05 (d, 1H), 2.91 (dd, 1H), 2.66-2.71 (m, 2H), 1.97-2.04 (m, 1H), 1.85-1.88 (m, 2H), 1.65-1.71 (m, 2H), 1.53-1.58 (m, 1H). | 425.2 (M − 1) 427.2 (M + 1) (C₁₇H₂₂N₄O₇S) |
| 24. | SO₂OH | H | 1,2,3,4-tetrahydroisoquinoline, 3-substituted | (DMSO-d₆): δ 11.91 (s, 1H), 9.18 (br s, 1H), 7.19-7.27 (m, 4H), 4.33 (dd, 2H), 3.83-4.11 (m, 4H), 2.99-3.08 (m, 2H), 2.94 (d, 1H), 2.83 (dd, 1H), 2.02-2.05 (m, 1H), 1.86-1.90 (m, 1H), 1.65-1.76 (m, 2H). | 425.0 (M − 1) (C₁₇H₂₂N₄O₇S) |
| 25. | SO₂OH | H | 1-methyl-4,5,6-trihydropyrrolo[3,4-c]pyrazole | (DMSO-d₆): δ 11.86 (br s, 1H), 9.90 (br s, 1H), 7.29 (s, 1H), 4.89 (dd, 1H), 4.46 (dd, 2H), 4.12 (dd, 1H), 4.01-4.05 (m, 2H), 3.83 (d, 1H), 3.75 (s, 3H), 2.98 (dd, 2H), 1.96-2.06 (m, 1H), 1.86-1.99 (m, 1H), 1.63-1.77 (m, 2H). | 415.1 (M − 1) 417.1 (M + 1) (C₁₄H₂₀N₆O₇S) |

TABLE 1-continued

| Example No. | R1 | R2 | R3 | $^1$H-NMR (DMSO-d$_6$)/D$_2$O, δ values | Mass (ES-1) as free acid (MF) |
|---|---|---|---|---|---|
| 26. | SO$_2$OH | H | (pyrrolo-pyrazole structure) | — | 401.1 (M − 1)<br>403.1 (M + 1)<br>(C$_{13}$H$_{18}$N$_6$O$_7$S) |
| 27. | SO$_2$OH | H | (dihydroxy dihydropyridine structure) | — | 404.2 (M − 1)<br>(C$_{13}$H$_{17}$N$_4$O$_9$S) |
| 28. | SO$_2$OH | H | (2-hydroxyphenyl oxazoline structure) | (DMSO-d$_6$ D$_2$O exchange) δ 7.50-7.52 (m, 1H), 7.33-7.37 (m, 1H), 6.91-6.94 (m, 2H), 4.25-4.31 (m, 3H), 4.15-4.17 (m, 1H) 3.97-4.05 (m, 2H), 3.05-2.95 (dd, 3H), 2.05-.97 (m, 2H), 1.82-1.85 (m, 3H), 1.66-1.62 (m, 2H). | 457.2 (M + 1)<br>(C$_{17}$H$_{20}$N$_4$O$_9$S) |
| 29. | SO$_2$OH | H | (pyrrolidinyl oxazoline structure) | (DMSO-d$_6$) D$_2$O exchange) δ 7.41 (d, 1H), 4.20-4.14 (m, 3H), 4.02-3.99 (m, 2H), 3.86-3.82 (dd, 1H) 3.75-3.74 (m, 1H), 3.68-3.64 (dd, 1H), 3.21-3.02 (m, 4H) 2.93-2.90 (d, 1H) 2.24-2.19 (m, 2H), 2.00-1.68 (m, 7H) | 432.1 (M − 1)<br>434.2 (M + 1)<br>(C$_{15}$H$_{23}$N$_5$O$_8$S) |
| 30. | SO$_2$OH | H | (pyrrolidine structure) | (D$_2$O): δ 4.733 (m, 1H), 4.107 (d, 1H), 4.001 (d, 1H), 3.516-3.481(d, 1H), 3.371(4H, m), 3.240-3.210 (d, 1H), 2.258-2.220(1H, m), 2.130-1.936(3H, m), 1.897-1.712(2H, m). | 350.9 (M + 1)<br>(C$_{11}$H$_{18}$N$_4$O$_7$S) |
| 31. | SO$_2$OH | H | (pyrrolidine structure) | — | 350.9 (M + 1)<br>(C$_{11}$H$_{18}$N$_4$O$_7$S) |
| 32. | SO$_2$OH | H | (pyrrolidine structure) | — | 350.9 (M + 1)<br>(C$_{11}$H$_{18}$N$_4$O$_7$S) |
| 33. | SO$_2$OH | H | (cyano pyrrolidine structure) | (DMSO-d$_6$): δ 11.62 (s, 1H), 9.77 (br, 1H), 4.802-4.83 (q, 1H), 4.68(s, 1H), 4.001(s, 1H), 3.78-3.79 (d, 1H), 3.56-3.59(d, 1H), 3.12-3.16 (m, 1H), 3.07 (s, 2H), 2.55-2.61 (m, 1H), 2.43-2.44 (d, 1H), 2.40-2.41(d, 1H), 1.97-1.99 (m, 1H), 1.86-1.975 (m, 1H), 1.66-1.71 (m, 2H). | [ES−] 373.9<br>[ES+] 376.0<br>(C$_{12}$H$_{17}$N$_5$O$_7$S) |

TABLE 1-continued

| Example No. | R1 | R2 | R3 | ¹H-NMR (DMSO-d₆)/D₂O, δ values | Mass (ES-1) as free acid (MF) |
|---|---|---|---|---|---|
| 34. | SO₂OH | H | (2-cyano-4-methylpyrrolidinyl structure) | — | [ES−] 373.9 [ES+] 376.0 ($C_{12}H_{17}N_5O_7S$) |
| 35. | SO₂OH | H | (2-carboxamido-4-methylpyrrolidinyl structure) | (DMSO-d₆): δ 11.38 (s, 1H), 9.44 (bs, 1H), 8.49 (bs, 1H), 7.90 (s, 1H), 7.70 (s, 1H), 4.63 (s, 1H), 4.20 (s, 1H), 3.99 (s, 1H), 3.77-3.78 (d, 1H), 3.54-3.57 (d, 1H), 3.02-3.14 (m, 1H), 2.99-3.02 (d, 1H), 2.92-2.95 (d, 1H), 2.55-2.60 (m, 1H), 2.10-2.11 (d, 1H), 2.05-2.067 (m, 1H), 1.85 (m, 1H), 1.61-1.72 (m, 1H), 1.55-1.61 (m, 1H). | [ES−] 391.8 [ES+] 394.1 ($C_{12}H_{19}N_5O_8S$) |
| 36 | SO₂OH | H | (azetidin-3-yl structure) | (DMSO-d₆): δ 11.8 (bs, 1H), 8.85 (bs, 1H), 8.52 (bs, 1H), 4.73 (m, 1H), 4.17 (m, 2H), 4.00 (m, 3H), 3.79 (d, 1H), 2.91-3.02 (m, 2H), 2.00 (m, 1H), 1.86 (m, 1H), 1.64-1.71 (m, 2H). | [ES⁺] 336.9 ($C_{10}H_{16}N_4O_7S$) |
| 37. | SO₂OH | (piperidin-2-yl structure) | CH₃ | (DMSO-d₆): δ 8.2-8.24 (d, 2H), 4.02 (s, 1H), 3.730 (m, 1H), 3.561 (s, 3H), 3.18-3.37 (m, 3H), 2.72-2.78 (m, 3H), 2.48-2.56 (m, 2H), 1.95-1.96 (m, 2H), 1.726-1.787 (m, 3H), 1.55-1.59 (m, 2H), 1.07-1.17 (m, 2H). | 392.42 ($C_{14}H_{24}N_4O_7S$) |
| 38. | SO₂OH | (piperidin-3-yl structure) | CH₃ | (DMSO-d₆): δ 8.4 (bs, 1H), 8.08 (bs, 1H), 4.31 (bs, 1H), 4.01 (s, 1H), 3.6.2-3.72 (m, 4H), 3.44-3.48 (m, 1H), 3.23 (bs, 3H), 2.97 (d, 1H), 2.84 (bs, 2H), 1.76-1.89 (m, 6H), 1.22-1.33 (m, 2H). | [ES−] 391.3 [ES+] 393.3 ($C_{14}H_{24}N_4O_7S$) |
| 39. | SO₂OH | (pyrrolidin-2-ylmethyl structure) | CH₃ | (DMSO-d₆): δ 8.95 (bs, 1H), 8.38 (bs, 1H), 4.33 (m, 1H), 4.03 (m, 2H), 3.65-3.90 (m, 5H), 3.00-3.24 (m, 4H), 2.03-2.09 (m, 1H), 1.73-1.91 (m, 5H), 1.26-1.31 (m, 2H), | [ES⁻] 377.3, [ES⁺] 379.2 ($C_{13}H_{22}N_4O_7S$) |

TABLE 2

| 40. | SO₂OH | H | (aminoethyl structure) ·CF₃COOH | (DMSO-d₆): δ 11.64 (s, 1H), 7.78 (bs, 3H), 4.01 (s, 1H), 3.95 (t, 2H), 3.82 (d, 1H), 2.95-3.02 (m, 3H), 2.92 (d, 1H), 1.89-2.04 (m, 1H), 1.85-1.88 (m, 1H), 1.61-1.75 (m, 2H). | 323.1 ($C_9H_{16}N_4O_7S$) |
| 41. | SO₂OH | H | (guanidinoethyl structure) ·CF₃COOH | (DMSO-d₆): 8.18 (t, 1H), 7.59 (bs, 5H), 3.98 (s, 1H), 3.81 (t, 2H), 3.74 (d, 1H), 3.38 (t, 2H), 2.99-3.02 (d, 1H), 2.82-2.85 (d, 1H), 2.05-2.08 (dd, 1H), 1.84-1.86 (m, 1H), 1.56-1.69 (m, 2H). | 365.1 ($C_{10}H_{18}N_6O_7S$) |
| 42. | SO₂OH | H | (aminopropyl structure) ·CF₃COOH | (DMSO-d₆): δ 11.63 (s, 1H), 7.72 (bs, 3H), 4.00 (s, 1H), 3.88 (t, 2H), 3.75 (d, 1H), 2.95-3.00 (m, 4H), 1.99 (d, 1H), 1.78-1.92 (m, 3H), 1.62-1.73 (m, 2H). | 337 ($C_{10}H_{18}N_4O_7S$) |

TABLE 2-continued

| # | | | | NMR | MS / Formula |
|---|---|---|---|---|---|
| 43. | SO$_2$OH | H | •CF$_3$COOH (structure: H$_2$N-substituted chain with NH) | (DMSO-d$_6$): δ 11.79(br, 1H), 7.94-7.663(br, 5H), 4.02(s, 1H), 3.94 (m, 1H), 3.81(m, 1H), 3.05-2.95(dd, 2H), 2.75(m, 2H), 2.06-1.88 (m, 2H), 1.68(m, 2H), 1.50(m, 4H), 1.35(m, 2H). | (M − H, 3.94(−SO$_3$H) (C$_{13}$H$_{26}$N$_5$O$_7$S•C$_2$O$_2$F$_3$) |
| 44. | SO$_2$OH | H | H$_2$N-pyrrolidinium •CF$_3$COOH | (DMSO-d$_6$): δ 9.00 (bs, 2H), 8.05(bs, 3H), 3.98-4.07(m, 3H), 3.80-3.84(t, 2H), 3.45-3.50(dd, 1H), 3.15-3.20(m, 1H), 3.03-3.06(d, 1H), 2.93-2.96(d, 1H), 2.41-2.47(m, 1H), 2.01-2.05(m, 1H), 1.88-1.90(m, 1H), 1.52-1.75(m, 6 H). | 378.2 (C$_{12}$H$_{21}$N$_5$O$_7$S) |
| 45. | SO$_2$OH | H | piperazine •CF$_3$COOH | (DMSO-d$_6$): δ 11.9 (s, 1H), 9.00 (bs, 2H), 3.94-4.02 (s, 1H), 3.79-3.80 (m, 1H), 3.44-3.59 (m, 4H), 3.03-3.16 (m, 4H), 2.99 (s, 2H), 1.99-2.03 (m, 1H), 1.88-1.91 (m, 1H), 1.65-1.75 (m, 2H), 1.53-1.55 (m, 1H), 1.26-1.32 (m, 1H). | [ES$^-$] 378.2, [ES$^+$] 380.1 for free amine C$_{12}$H$_{21}$N$_5$O$_7$S•C$_2$HO$_2$F$_3$ |
| 46. | SO$_2$OH | | CH$_3$ (structure: piperazine •CF$_3$COOH) | (DMSO-d$_6$): δ 8.2-9.6 (bs, 3H), 4.38 (m, 1H), 4.01 (m, 2H), 3.69 (m, 4H), 3.33-3.58(m, 4H), 2.92-3.31(m, 5H), 2.70-2.91(m, 1H), 1.50-1.95(m, 4H). | C$_{13}$H$_{24}$N$_5$O$_7$S•C$_2$O$_2$F$_3$ [ES$^-$] 392.2, [ES$^+$] 394.3 |

TABLE 3

| # | | | | NMR | MS / Formula |
|---|---|---|---|---|---|
| 47. | SO$_2$ONa | CH$_3$ | CH$_3$ | (DMSO-d$_6$): δ 4.38 (m, 1H), 4.15-4.20 (m, 2H), 3.58-3.78 (m, 4H), 3.15-3.42 (m, 4H), 1.83-2.04δ (m, 4H) | [ES$^-$] 308.1, [ES$^+$] 310.1 for free acid (C$_9$H$_{14}$N$_3$O$_7$S•Na) |
| 48. | SO$_2$ONa | H | CH$_3$ | (DMSO-d$_6$): δ 11.39 (s, 1H), 3.97 (s, 1H), 3.66 (d, 1H), 3.57 (s, 3H), 2.99 (dd, 2H), 1.95-1.97 (m, 1H), 1.79-1.88 (m, 1H), 1.62-1.72 (m, 2H). | 294 for free acid C$_8$H$_{12}$N$_3$O$_7$S•Na |
| 49. | SO$_2$ONa | H | H | (D$_2$O): δ 4.10-4.22 (m, 2H), 3.52-3.64 (m, 1H), 3.22-3.26 (m, 1H), 1.70-2.10 (s, 4H). | 280.01 (M − 1) C$_7$H$_{11}$N$_3$O$_7$S |
| 50. | SO$_2$ONa | H | N-methylpyrazolyl | (DMSO-d$_6$ D$_2$O exchange): δ 7.32 (d, 1H), 6.29 (d, 1H), 4.83 (s, 2H), 3.95-3.91 (m, 4H) 3.76-3.66 (m, 2H), 2.98-2.88 (dd, 2H), 1.95-1.93 (m, 1H), 1.82 (m, 1H), 1.67-1.62 (m, 2H). | 374.2 (M − 1) 376.3 (M + 1) (C$_{12}$H$_{16}$N$_5$O$_7$S•Na) |
| 51. | SO$_2$ONa | CH$_3$ | H | — | 294 for free acid C$_8$H$_{12}$N$_3$O$_7$S•Na |

Biological Activity

The biological activity of representative compounds according to the invention against various bacterial strains was investigated. In a typical study, overnight grown bacterial cultures were diluted appropriately and inoculated on the agar media containing doubling dilutions of the test compounds. Observation for growth or no growth was performed after 16-20 hours of incubation at 35±2° C. in ambient air. The overall procedure was performed as per Clinical and Laboratory Standards Institute (CLSI) recommendations (Clinical and Laboratory Standards Institute (CLSI), Performance Standards for Antimicrobial Susceptibility Testing, 20th Informational Supplement, M 100-S20, Volume 30, No. 1, 2010).

Table 4 describes antibacterial activity of representative compounds according to the invention against various Multi Drug Resistant (MDR) Gram-negative bacterial strains expressing various ESBLs. The activities are expressed as MICs (mcg/ml). For comparison, the activity of several known antibacterial agents (for example, Ceftazidime, Aztreonam, Imipenem, Ciprofloxacin and Tigecycline) are also included. As can be seen, the representative compounds according to the invention exhibit antibacterial activity against various MDR strains.

TABLE 4

Comparative antibacterial activity of representative compounds according to the invention against various Multi Drug Resistant (MDR) Gram negative strains (expressed as MICs (mcg/ml).

| | | Class A ESBL | | Class C ESBL | | P. aeruginosa | |
|---|---|---|---|---|---|---|---|
| Sr. | Compound | E. Coli W 13353 | E. Coli W 13351 | E. Coli W 13352 | E. Coli M 50 | E. Coli H 483 | Ps 21 | Ps 32 |
| 1. | Ceftazidime | 32 | 32 | >32 | >32 | >32 | >32 | >32 |
| 2. | Aztreonam | >32 | >32 | >32 | >32 | >32 | 8 | 8 |
| 3. | Imipenem | 0.25 | 0.25 | 0.25 | 0.5 | 1 | >32 | >32 |
| 4. | Ciprofloxacin | >32 | 0.5 | 0.12 | >32 | >32 | 32 | 0.12 |
| 5. | Tigecyclin | 1 | 1 | 0.25 | 0.5 | 0.5 | 16 | 16 |
| 6. | Example 1 | 0.5 | 1 | 1 | 0.5 | >32 | >32 | >32 |
| 7. | Example 2 | 1 | 2 | 2 | 1 | >32 | >32 | >32 |
| 8. | Example 3 | 8 | 16 | 16 | 8 | >32 | >32 | >32 |
| 9. | Example 4 | 8 | 8 | 8 | 8 | >32 | >32 | >32 |
| 10. | Example 17 | 0.5 | 1 | 1 | 0.5 | >32 | >32 | >32 |
| 11. | Example 18 | 0.5 | 1 | 1 | 1 | >32 | >32 | >32 |
| 12. | Example 19 | 4 | 8 | 16 | 8 | >32 | >32 | >32 |
| 13. | Example 30 | 4 | 8 | 8 | 4 | >32 | >32 | >32 |
| 14. | Example 33 | 4 | 4 | >32 | 4 | >32 | >32 | >32 |
| 15. | Example 35 | 4 | 16 | 8 | 8 | >32 | >32 | >32 |

The invention claimed is:

1. A method for treating bacterial infection, comprising orally administering to a subject in need thereof a pharmaceutically effective amount of (a) at least one antibacterial agent selected from the group consisting of cefpodoxime, ceftibuten, cefuroxime, cefixime and pharmaceutically acceptable salts thereof; and (b) at least one compound selected from a group consisting of:

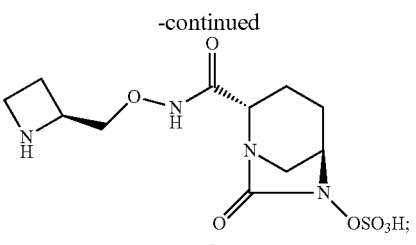

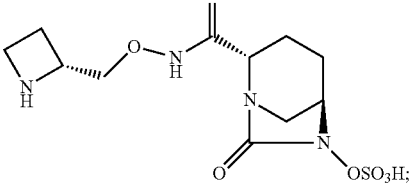

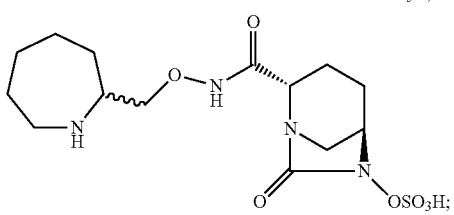

-continued

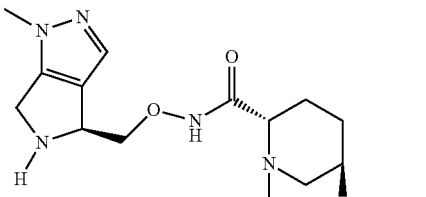

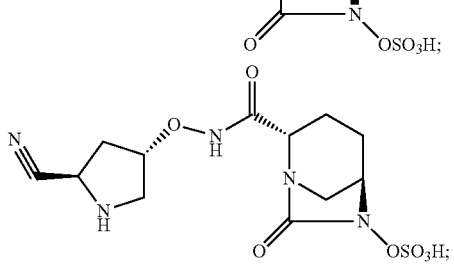

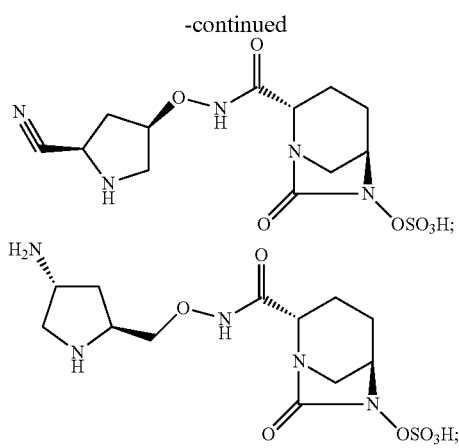

and a stereoisomer; and a pharmaceutically acceptable salt thereof.

2. The method according to claim 1, wherein the compound is administered as a sodium salt.

3. A method for treating bacterial infection, comprising orally administering to a subject in need thereof a pharmaceutical composition comprising: (a) at least one antibacterial agent selected from the group consisting of cefpodoxime, ceftibuten, cefuroxime, cefixime and pharmaceutically acceptable salts thereof; (b) one or more pharmaceutically acceptable excipients; and (c) at least one compound selected from a group consisting of:

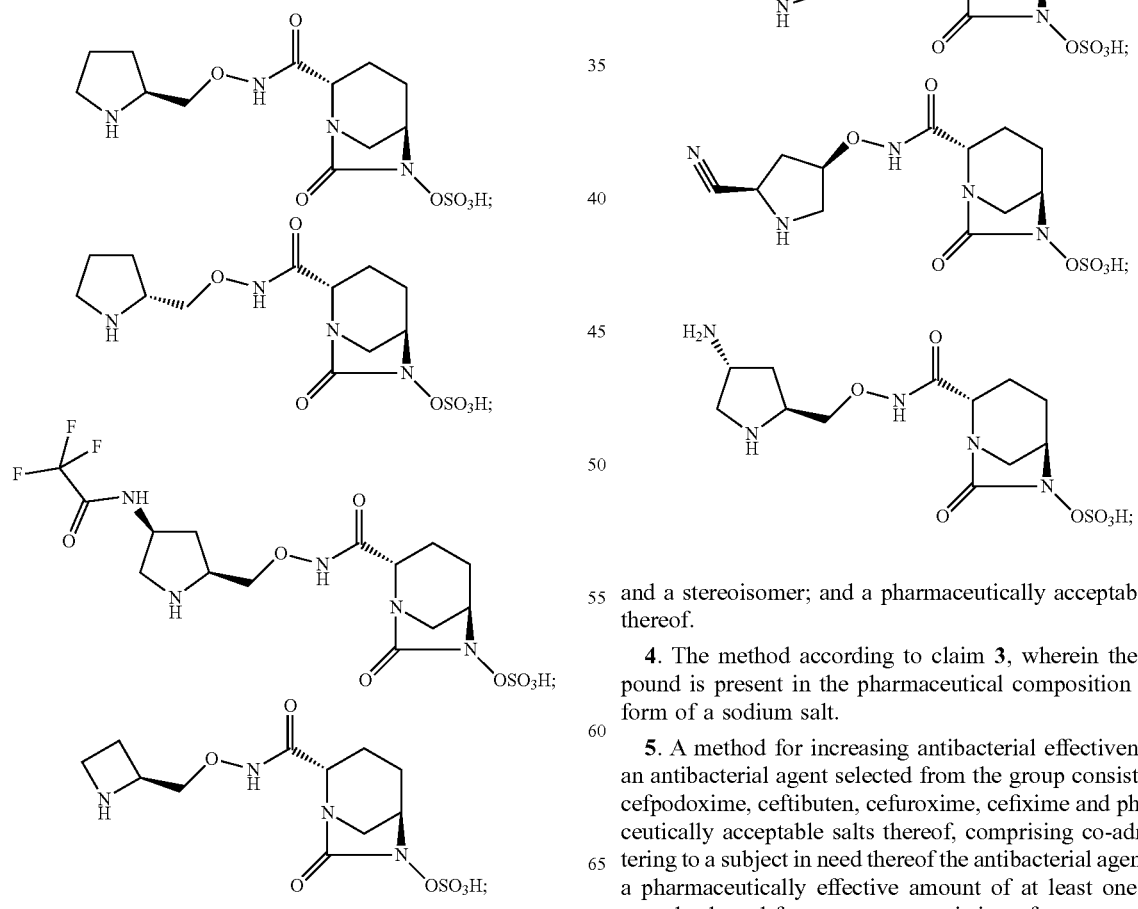

and a stereoisomer; and a pharmaceutically acceptable salt thereof.

4. The method according to claim 3, wherein the compound is present in the pharmaceutical composition in the form of a sodium salt.

5. A method for increasing antibacterial effectiveness of an antibacterial agent selected from the group consisting of cefpodoxime, ceftibuten, cefuroxime, cefixime and pharmaceutically acceptable salts thereof, comprising co-administering to a subject in need thereof the antibacterial agent with a pharmaceutically effective amount of at least one compound selected from a group consisting of:

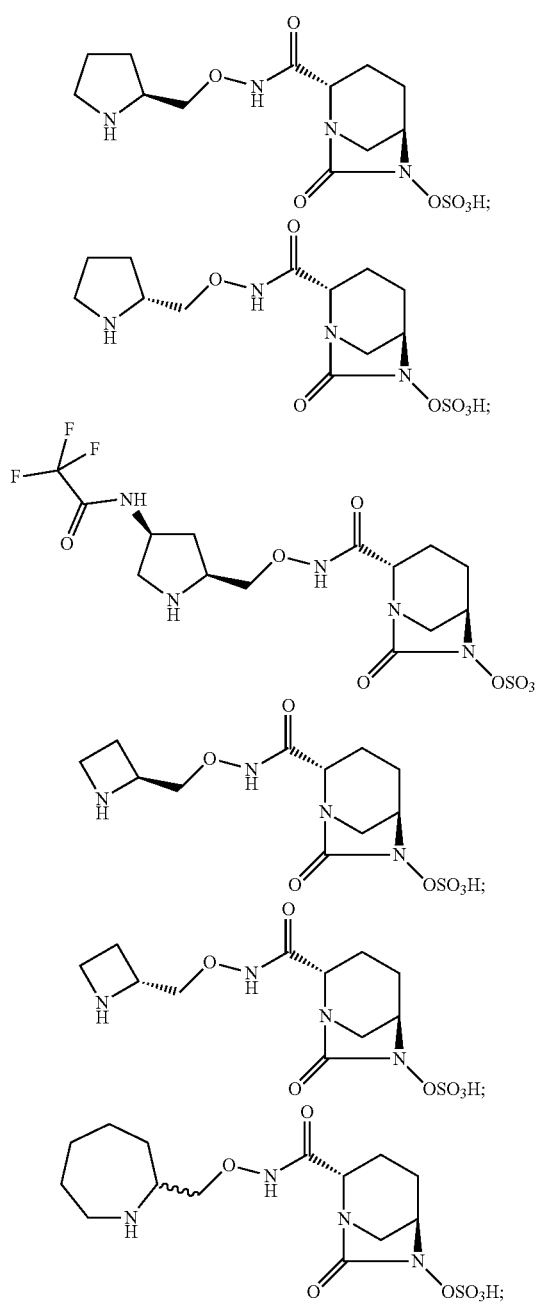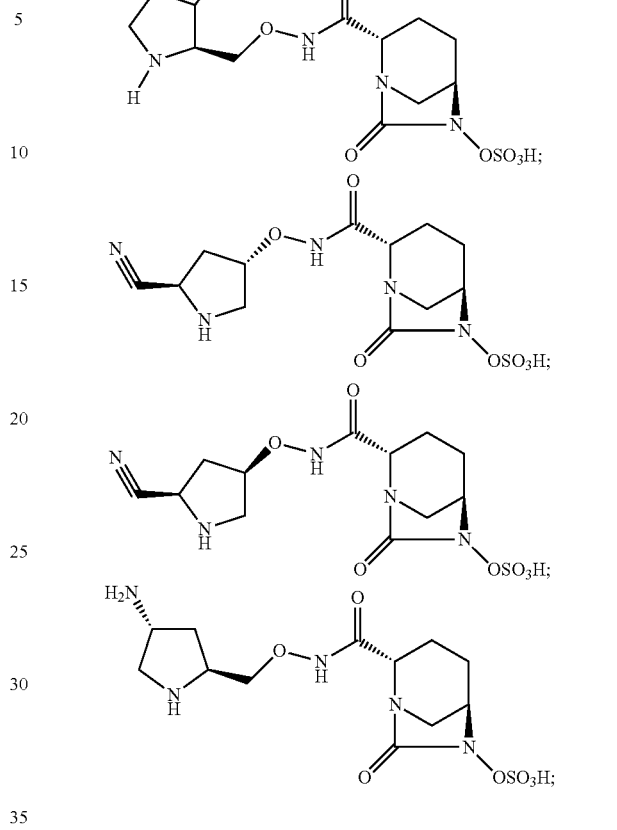

and a stereoisomer; and a pharmaceutically acceptable salt thereof.

6. The method according to claim 1, wherein the infection is caused by a bacteria producing one or more beta-lactamase enzymes.

7. The method according to claim 2, wherein the infection is caused by a bacteria producing one or more beta-lactamase enzymes.

8. The method according to claim 3, wherein the infection is caused by a bacteria producing one or more beta-lactamase enzymes.

9. The method according to claim 4, wherein the infection is caused by a bacteria producing one or more beta-lactamase enzymes.

* * * * *